(12) United States Patent
Kierse et al.

(10) Patent No.: US 10,730,743 B2
(45) Date of Patent: Aug. 4, 2020

(54) GAS SENSOR PACKAGES

(71) Applicant: Analog Devices Global Unlimited Company, Hamilton (BM)

(72) Inventors: Oliver J. Kierse, Killaloe (IE); Rigan McGeehan, Limerick (IE); Alfonso Berduque, Crusheen (IE); Donal Peter McAuliffe, Raheen (IE); Raymond J. Speer, Dalkey (IE); Brendan Cawley, Patrickswell (IE); Brian J. Coffey, Ennis (IE); Gerald Blaney, Limerick (IE)

(73) Assignee: Analog Devices Global Unlimited Company, Hamilton (BM)

( * ) Notice: Subject to any disclaimer, the term of this patent is extended or adjusted under 35 U.S.C. 154(b) by 0 days.

(21) Appl. No.: 16/159,477

(22) Filed: Oct. 12, 2018

(65) Prior Publication Data

US 2019/0135614 A1    May 9, 2019

Related U.S. Application Data

(60) Provisional application No. 62/582,229, filed on Nov. 6, 2017.

(51) Int. Cl.
*H01L 23/02* (2006.01)
*B81B 7/00* (2006.01)
(Continued)

(52) U.S. Cl.
CPC .......... *B81B 7/0051* (2013.01); *B81B 7/0061* (2013.01); *B81C 1/00269* (2013.01);
(Continued)

(58) Field of Classification Search
CPC ..... H01L 2924/16195; H01L 2924/181; H01L 2924/19105; H01L 25/0655
(Continued)

(56) References Cited

U.S. PATENT DOCUMENTS

| 4,671,852 A | 6/1987 | Pyke |
| 5,313,365 A | 5/1994 | Pennisi et al. |

(Continued)

FOREIGN PATENT DOCUMENTS

| CN | 1728365 A | 2/2006 |
| CN | 1877989 | 12/2006 |

(Continued)

OTHER PUBLICATIONS

Chinese Office Action dated Aug. 11, 2016 for Chinese Patent Application No. 201410454353.9, 3 pages.
(Continued)

*Primary Examiner* — S. V. Clark
(74) *Attorney, Agent, or Firm* — Knobbe, Martens, Olson & Bear, LLP

(57) ABSTRACT

A gas sensor package is disclosed. The gas sensor package can include a housing defining a first chamber and a second chamber. An electrolyte can be provided in the first chamber. A gas inlet can provide fluid communication between the second chamber and the outside environs. The gas inlet can be configured to permit gas to enter the second chamber from the outside environs. An integrated device die can be mounted to the housing. The integrated device die can comprise a sensing element configured to detect the gas. The integrated device die can have a first side exposed to the first chamber and a second side exposed to the second chamber, with the first side opposite the second side.

20 Claims, 13 Drawing Sheets

(51) Int. Cl.

| | |
|---|---|
| *G01N 33/00* | (2006.01) |
| *H01L 23/00* | (2006.01) |
| *H01L 23/31* | (2006.01) |
| *G01N 27/404* | (2006.01) |
| *H01L 25/065* | (2006.01) |
| *B81C 1/00* | (2006.01) |
| *H01L 23/055* | (2006.01) |
| *H01L 23/24* | (2006.01) |
| *H01L 23/49* | (2006.01) |
| *H01L 23/498* | (2006.01) |
| *H01L 23/50* | (2006.01) |

(52) U.S. Cl.
CPC ....... *G01N 27/404* (2013.01); *G01N 33/0036* (2013.01); *H01L 23/00* (2013.01); *H01L 23/055* (2013.01); *H01L 23/24* (2013.01); *H01L 23/3185* (2013.01); *H01L 23/49* (2013.01); *H01L 23/49838* (2013.01); *H01L 23/50* (2013.01); *H01L 24/48* (2013.01); *H01L 25/0655* (2013.01); *B81B 2201/0214* (2013.01); *B81B 2207/012* (2013.01); *B81C 2203/0154* (2013.01); *H01L 24/29* (2013.01); *H01L 24/32* (2013.01); *H01L 24/45* (2013.01); *H01L 2224/131* (2013.01); *H01L 2224/26175* (2013.01); *H01L 2224/293* (2013.01); *H01L 2224/2929* (2013.01); *H01L 2224/32014* (2013.01); *H01L 2224/32225* (2013.01); *H01L 2224/45124* (2013.01); *H01L 2224/45144* (2013.01); *H01L 2224/48091* (2013.01); *H01L 2224/48227* (2013.01); *H01L 2224/48245* (2013.01); *H01L 2224/73265* (2013.01); *H01L 2224/83138* (2013.01); *H01L 2224/83851* (2013.01); *H01L 2924/15313* (2013.01); *H01L 2924/16195* (2013.01); *H01L 2924/181* (2013.01); *H01L 2924/182* (2013.01); *H01L 2924/19105* (2013.01)

(58) Field of Classification Search
USPC .................................. 257/678, 682, 690, 704
See application file for complete search history.

(56) References Cited

U.S. PATENT DOCUMENTS

| | | | |
|---|---|---|---|
| 5,666,127 A | 9/1997 | Kochiyama et al. | |
| 5,870,482 A | 2/1999 | Loeppert et al. | |
| 6,075,239 A | 6/2000 | Aksyuk et al. | |
| 6,765,287 B1 | 7/2004 | Lin | |
| 6,800,930 B2 | 10/2004 | Jackson et al. | |
| 6,803,559 B2 | 10/2004 | Hsu et al. | |
| 6,879,429 B2 | 4/2005 | Wong et al. | |
| 6,894,502 B2 | 5/2005 | Feng et al. | |
| 7,130,177 B2 | 10/2006 | Aizawa et al. | |
| 7,208,832 B2 | 4/2007 | Yamagata | |
| 7,242,089 B2 | 7/2007 | Minervini | |
| D575,056 S | 8/2008 | Tan | |
| 7,550,834 B2 | 6/2009 | Yu et al. | |
| 7,648,911 B2 | 1/2010 | Pagaila et al. | |
| 7,691,747 B2 | 4/2010 | Lin et al. | |
| 7,719,427 B2 | 5/2010 | Hsiung et al. | |
| 7,723,831 B2 | 5/2010 | Kwang et al. | |
| 7,855,429 B2 | 12/2010 | Ishida et al. | |
| 7,875,942 B2 | 1/2011 | Cortese et al. | |
| 7,898,043 B2 | 3/2011 | Ziglioli et al. | |
| 8,101,898 B2 | 1/2012 | Koste et al. | |
| 8,199,939 B2 | 6/2012 | Suvanto et al. | |
| 8,274,147 B2 | 9/2012 | Rofougaran et al. | |
| 8,280,207 B2 | 10/2012 | Pinguet et al. | |
| 8,300,870 B2 | 10/2012 | Lee et al. | |
| 8,339,798 B2 | 12/2012 | Minoo et al. | |
| 8,350,382 B2 | 1/2013 | Furgut et al. | |
| 8,362,589 B2 | 1/2013 | Quinn | |
| 8,368,654 B2 | 2/2013 | Rosenblatt et al. | |
| 8,390,083 B2 | 3/2013 | O'Donnell et al. | |
| 8,395,252 B1 | 3/2013 | Yang | |
| 8,402,666 B1 | 3/2013 | Hsu et al. | |
| 8,436,690 B2 | 5/2013 | McCraith et al. | |
| 8,436,698 B2 | 5/2013 | Rogers | |
| 8,569,861 B2 | 10/2013 | O'Donnell et al. | |
| 8,574,413 B2 | 11/2013 | Mosley et al. | |
| 8,577,063 B2 | 11/2013 | Yang | |
| 8,637,943 B1 | 1/2014 | Yang | |
| 8,754,643 B2 | 6/2014 | Gugel et al. | |
| 8,779,532 B2 | 7/2014 | O'Donnell et al. | |
| 8,847,340 B2 | 9/2014 | Baldo et al. | |
| 8,852,513 B1* | 10/2014 | Speer | G01N 33/0014 204/424 |
| 8,853,799 B2 | 10/2014 | O'Donnell et al. | |
| 8,890,285 B2 | 11/2014 | O'Donnell et al. | |
| 8,890,286 B2 | 11/2014 | O'Donnell et al. | |
| 8,957,497 B2 | 2/2015 | O'Donnell et al. | |
| 9,041,150 B2 | 5/2015 | O'Donnell et al. | |
| 9,063,084 B1 | 6/2015 | Lin et al. | |
| 9,267,915 B2 | 2/2016 | O'Donnell et al. | |
| 9,618,490 B2 | 4/2017 | Paik et al. | |
| 2004/0000713 A1 | 1/2004 | Yamashita et al. | |
| 2004/0190254 A1 | 9/2004 | Hu et al. | |
| 2005/0156584 A1 | 7/2005 | Feng | |
| 2005/0253244 A1 | 11/2005 | Chang | |
| 2006/0139883 A1 | 6/2006 | Hu et al. | |
| 2006/0258053 A1 | 11/2006 | Lee et al. | |
| 2006/0261460 A1 | 11/2006 | Sato et al. | |
| 2006/0266098 A1* | 11/2006 | Eickhoff | G01N 27/4163 73/1.06 |
| 2006/0283252 A1 | 12/2006 | Liu et al. | |
| 2007/0053504 A1 | 3/2007 | Sato et al. | |
| 2007/0071268 A1 | 3/2007 | Harney et al. | |
| 2007/0187826 A1 | 8/2007 | Shim et al. | |
| 2007/0202627 A1 | 8/2007 | Minervini | |
| 2007/0210423 A1 | 9/2007 | Hsu | |
| 2007/0246806 A1 | 10/2007 | Ong et al. | |
| 2007/0246813 A1 | 10/2007 | Ong et al. | |
| 2007/0278601 A1 | 12/2007 | Goodelle et al. | |
| 2007/0296065 A1 | 12/2007 | Yew et al. | |
| 2008/0054431 A1 | 3/2008 | Wang et al. | |
| 2008/0075309 A1 | 3/2008 | Chen et al. | |
| 2008/0175425 A1 | 7/2008 | Roberts et al. | |
| 2008/0217766 A1 | 9/2008 | Minervini | |
| 2008/0234599 A1 | 9/2008 | Chiao et al. | |
| 2008/0265421 A1 | 10/2008 | Brunnbauer et al. | |
| 2008/0304681 A1 | 12/2008 | Langlois et al. | |
| 2009/0008792 A1 | 1/2009 | Ko et al. | |
| 2009/0029492 A1 | 1/2009 | Tu et al. | |
| 2009/0039492 A1 | 2/2009 | Kang et al. | |
| 2009/0079065 A1 | 3/2009 | Furgut et al. | |
| 2009/0170242 A1 | 7/2009 | Lin et al. | |
| 2009/0194829 A1 | 8/2009 | Chung et al. | |
| 2009/0200620 A1 | 8/2009 | Omura et al. | |
| 2009/0202089 A1 | 8/2009 | Zhang et al. | |
| 2009/0204250 A1 | 8/2009 | Potyrailo et al. | |
| 2009/0261460 A1 | 10/2009 | Kuan et al. | |
| 2009/0283871 A1 | 11/2009 | Chang et al. | |
| 2009/0302437 A1 | 12/2009 | Kim et al. | |
| 2009/0321930 A1 | 12/2009 | Marcoux | |
| 2010/0032748 A1 | 2/2010 | Edwards | |
| 2010/0044704 A1 | 2/2010 | Male et al. | |
| 2010/0052630 A1 | 3/2010 | Chen | |
| 2010/0086146 A1 | 4/2010 | Gong et al. | |
| 2010/0134139 A1 | 6/2010 | Chen et al. | |
| 2010/0142744 A1 | 6/2010 | Rombach et al. | |
| 2010/0155863 A1 | 6/2010 | Weekamp | |
| 2010/0171203 A1 | 7/2010 | Chen et al. | |
| 2010/0181643 A1 | 7/2010 | Kothandaraman et al. | |
| 2010/0193905 A1 | 8/2010 | Kim et al. | |
| 2010/0284553 A1 | 11/2010 | Conti et al. | |
| 2011/0023929 A1 | 2/2011 | Edwards | |
| 2011/0057273 A1 | 3/2011 | O'Donnell et al. | |
| 2011/0101537 A1 | 5/2011 | Barth | |
| 2011/0108933 A1 | 5/2011 | Nakatani | |

(56) References Cited

U.S. PATENT DOCUMENTS

| | | | |
|---|---|---|---|
| 2011/0140703 | A1 | 6/2011 | Chiao et al. |
| 2011/0198714 | A1 | 8/2011 | Yang |
| 2011/0199057 | A1 | 8/2011 | Ivanov et al. |
| 2013/0037909 | A1 | 2/2013 | French |
| 2013/0119509 | A1 | 5/2013 | Farooq et al. |
| 2013/0250532 | A1 | 9/2013 | Bryzek et al. |
| 2013/0273693 | A1 | 10/2013 | Haba et al. |
| 2013/0299924 | A1 | 11/2013 | Weber et al. |
| 2014/0014480 | A1 | 1/2014 | Anderson et al. |
| 2014/0026649 | A1 | 1/2014 | O'Donnell et al. |
| 2014/0034104 | A1 | 2/2014 | O'Donnell et al. |
| 2014/0035630 | A1 | 2/2014 | O'Donnell et al. |
| 2014/0103540 | A1 | 4/2014 | Ching et al. |
| 2014/0162393 | A1 | 6/2014 | Yang |
| 2014/0250975 | A1* | 9/2014 | Kane ................. G01N 1/2205 73/23.31 |
| 2014/0311905 | A1* | 10/2014 | Stetter ................. B01J 31/06 204/424 |
| 2015/0075257 | A1 | 3/2015 | Paik et al. |
| 2015/0075258 | A1 | 3/2015 | Paik et al. |
| 2015/0177171 | A1 | 6/2015 | Kim et al. |
| 2015/0198551 | A1 | 7/2015 | Jun et al. |
| 2015/0247818 | A1* | 9/2015 | Silvester ............ G01N 27/4045 205/793 |
| 2015/0362451 | A1 | 12/2015 | Hunziker et al. |
| 2016/0047774 | A1* | 2/2016 | Teysseyre .......... G01N 27/4065 205/775 |
| 2018/0059044 | A1 | 3/2018 | Berduque et al. |
| 2019/0227024 | A1* | 7/2019 | Bhat ................. G01N 27/304 |
| 2019/0227026 | A1* | 7/2019 | Bhat ................. G01N 27/304 |

FOREIGN PATENT DOCUMENTS

| | | |
|---|---|---|
| CN | 101409279 | 4/2009 |
| CN | 201490184 | 5/2010 |
| EP | 0015322 | 9/1980 |
| EP | 1732215 | 12/2006 |
| EP | 2086015 | 8/2009 |
| EP | 2765410 A1 | 8/2014 |
| EP | 2857349 A3 | 5/2015 |
| JP | S60-012780 | 1/1985 |
| JP | H04-152664 | 5/1992 |
| JP | H05-258925 | 10/1993 |
| JP | H10-051017 | 2/1998 |
| JP | 2002-111041 | 4/2002 |
| JP | 2002-246514 | 8/2002 |
| JP | 2004-207540 | 7/2004 |
| JP | 2004-349537 | 12/2004 |
| JP | 2005-283389 | 10/2005 |
| JP | 2005-353867 | 12/2005 |
| JP | 2006-245311 | 9/2006 |
| JP | 2006-344737 | 12/2006 |
| JP | 2006-352136 | 12/2006 |
| JP | 2007-103413 | 4/2007 |
| JP | 2007-234913 | 9/2007 |
| JP | 2008-017421 | 1/2008 |
| JP | 2008-173462 | 7/2008 |
| JP | 2009-081100 | 4/2009 |
| JP | 2009-081160 | 4/2009 |
| JP | 2009-200189 | 9/2009 |
| JP | 2010-087021 | 4/2010 |
| JP | 2010-251662 | 11/2010 |
| KR | 10-0537093 | 12/2005 |
| KR | 2006-0045375 | 5/2006 |
| KR | 2009-0117004 | 11/2009 |
| KR | 10-2010-0112699 | 10/2010 |
| WO | WO 96/02438 A1 | 2/1996 |
| WO | WO 97/44707 | 11/1997 |
| WO | WO 2005/101476 | 10/2005 |
| WO | WO 2007/129787 A1 | 11/2007 |
| WO | WO 2010/053997 | 5/2010 |
| WO | WO 2010/100929 | 9/2010 |
| WO | WO 2010/117874 | 10/2010 |
| WO | WO 2010/136919 | 12/2010 |
| WO | WO 2011/103720 A1 | 9/2011 |
| WO | WO 2016/015028 A1 | 1/2016 |
| WO | WO 2017/099963 A1 | 6/2017 |

OTHER PUBLICATIONS

Chinese Office Action dated Dec. 21, 2015 for Chinese Patent Application No. 201410454357.7, filed Sep. 9, 2014, 10 pages.
Chinese Office Action dated Dec. 28, 2015 for Chinese Patent Application No. 201410454354.3, filed Sep. 9, 2014. 5 pages.
Chinese Office Action dated Dec. 30, 2013 for Chinese Patent Application No. 201110433902.0, filed Dec. 22, 2011. 6 pages.
Chinese Office Action dated Feb. 3, 2016 for Chinese Patent Application No. 201410454358.1, filed Sep. 9, 2014.
Chinese Office Action dated Jul. 18, 2016 for Chinese Patent Application No. 201410454357.7, 5 pages.
Chinese Office Action dated Mar. 2, 2016 for Chinese Patent Application No. 201410454353.9, filed Sep. 9, 2014.
Chinese Office Action dated Sep. 13, 2016 for Chinese Patent Application No. 201410454354.3, 6 pages.
Chou, J., Chapter 2: Electrochemical Sensors, Hazardous Gas Monitors, 1000 McGraw-Hill, pp. 27-35.
Decision of Rejection dated Jan. 18. 2016 for Japanese Patent Application No. 2011-279492, 8 pages and 8 page translation.
E. Meng et al., "Polymer MEMS for Micro Fluid Delivery Systems", American Chemical Society (ACS) Polymer MEMS Symposia, New York, New York, USA, Sep. 2003. (two pages).
European Communication under Rule 63(1) dated Oct. 8, 2015 in European Patent Application No. 15 170 129.9, 3 pages.
European Office Action dated Jan. 18, 2016 for European Patent Application No. 11 192 789.3, 5 pages.
Extended European Search Report dated Mar. 26, 2012, in European Application No. 11192789.3.
Extended European Search Report issued in application No. 18204196.2 dated Feb. 13, 2019.
Extended European Search Report dated Mar. 17, 2016 for European Patent Application No. 15170129.9. 12 pages.
Extended Search Report dated May 8, 2015 in European Patent Application No. 15151494.0, 7 pages.
F. Roozeboom et al., "System-in-Package Integration of Passives using 3D Through-Silicon Vias", Solid State Technology, May 2008, vol. 51, No. 5, pp. 38-47.
H.B. Fan et al., "Prediction of Delamination in a Bi-material System based on Free-Edge Energy Evaluation", Proceedings of the 53rd IEEE Electronic Components and Technology Conference, May 2003, pp. 1160-1164.
Hagleitner, et al., "Smart single-chip gas sensor microsystem", Nature 414, Nov. 15, 2001, 3 pages.
Japanese Office Action dated Feb. 10, 2016 for Japanese Patent Application No. 2015-079984, filed Apr. 9, 2015, 4 pages and 4 page translation.
Japanese Office Action dated Feb. 2, 2015 for Japanese Patent Application No. 2011-279492, filed on Dec. 21, 2011. 3 pages, 3 page translation.
Japanese Office Action dated Feb. 26, 2013 for Japanese Patent Application No. 2011279492: filed Dec. 21, 2011. 3 pages, 3 page translation.
Japanese Office Action dated Jun. 29, 2015 for Japanese Patent Application No. 2015-079984, filed Apr. 9, 2015. 3 pages, 3 page translation.
Japanese Office Action dated Mar. 31, 2014 for Japanese Patent Application No. 2011-279492, filed Dec. 21, 2011. 3 pages, 3 page translation.
K. Wang et al., "Interfacial Shear Stress, Peeling Stress and Die Cracking Stress in Trilyaer Electronic Assemblies", IEEE 7th Intersociety Conference on Thermomechanical Phenomena in Electronic Systems, May 2000, vol. 2, pp. 56-64.
Kim, et al., "Hydrogel-Based Integrated Antenna-pH Sensor", IEEE Sensors Conference, 2007, pp. 695-698.
Korean Office Action dated Jun. 17, 2013 for Korean Patent Application No. 10-2011-0139346 filed Dec. 21, 2011. 6 pages, 6 page translation.

(56) References Cited

OTHER PUBLICATIONS

M. Berger, "Polymer Carpets—A New Class of Nanomaterials for NEMS and MEMS", Nanowerk, Sep. 2, 2010. (retrieved from http://www.nanowerk.com/spotlight/spotid=17875.php).

M. Duplessis et al., "Physical Implementation of 3D Integrated Solenoids within Silicon Substrate for Hybrid IC Applications", IEEE European Microwave Conference, Oct. 2009, pp. 1006-1009.

Maseeh, et al., "A Novel Silicon Micro Amperometric Gas Sensor", IEEE 1991, pp. 359-362.

Massachusetts Institute of Technology, "Funneling Solar Energy: Antenna Made of Carbon Nanotubes Could Make Photovoltaic Cells More Efficient", ScienceDaily, Sep. 13, 2010. (retrieved from http://www.sciencedaily.com/releases/2010/09/100912151548.htm).

Notice of Allowance dated Dec. 26, 2013 for Korean Patent Application No. 10-2011-0139346 filed Dec. 21, 2011. 2 pages, 1 page translation.

Office Action dated Jul. 3, 2015 for Chinese Application No. 201410454353.9, 4 pages.

Office Action dated Mar. 17, 2016 for Taiwanese Patent Application No. 103131989. 5 pages.

Search Report dated Nov. 30, 2015 in Taiwanese Patent Application No. 103131988, 4 pages (.

T.D. Moore, "Peeling Stress Analyzed for Resistance to Delamination—Application to Multiple Thin Films on a Thick Substrate", IEEE 9th Intersociety Conference on Thermomechanical Phenomena in Electronic Systems, Jun. 2004, vol. 2, pp. 330-335.

Taiwanese Office Action dated Jul. 11, 2014 for Taiwanese Patent Application No. 100146568, filed on Dec. 15, 2011. 4 pages, 3 page translation.

Taiwanese Office Action dated Nov. 26, 2015 for Taiwan Patent Application No. 103131988, filed Sep. 16, 2014. 7 pages with translation.

Taiwanese Search Report dated Jun. 11, 2015 for Taiwanese Patent Application No. 104113577, filed Dec. 15, 2011, 1 page and 1 page translation.

Translation of Office Action dated Oct. 26, 2015 in Japanese Patent Application No. 2015-079984, 6 pages.

University of Southern California, "Graphene Organic Photovoltaics: Flexible Material Only a Few Atoms Thick May Offer Cheap Solar Power", ScienceDaily, Jul. 24, 2010. (retrieved from http://www.sciencedaily.com/releases/2010/07/100723095430.htm).

Website for Goldpoint pH Sensor orp202g-2 having 2014 copyright date, http://www.igpg.com.cn/Products/Online_pH_ORP_Sensor2/75.html (accessed Jun. 10, 2016).

Website related to Andose pH sensor Glass ORP/pH sensor, http://www.aliexpress.com/store/product/Glass-PH-sensor-PH-electrode-for-pipe-on-stallation-ph-G2008/1040787_32259217887.html (accessed Jun. 10, 2016).

Y. Luo et al., "An Improved Estimate for Thermal Stresses in Multi-Layer Assemblies", IEEE 11th Intersociety Conference on Thermal and Thermomechanical Phenomena in Electronic Systems, May 2008, pp. 842-852.

\* cited by examiner

GAS SENSOR PACKAGES

CROSS-REFERENCE TO RELATED APPLICATIONS

This application claims priority to U.S. Provisional Patent Application No. 62/582,229, filed Nov. 6, 2017, the entire contents of which are hereby incorporated by reference herein in their entirety and for all purposes.

BACKGROUND

Field

The field relates to gas sensor packages.

Description of the Related Art

Gas sensor devices are used in many industries to detect the presence of and to identify gases. For example, in the automotive industry, it can be important to detect and/or identify various types of gases during operation of a vehicle. In petrochemical or other industrial applications, it can also be important to detect and/or identify gases. However, conventional gas sensor devices are expensive, large, and difficult to integrate with surface mount technology. Accordingly, there remains a continuing need for improved gas sensors.

SUMMARY

In one aspect, a gas sensor package is disclosed. The gas sensor includes a housing defining a first chamber and a second chamber. The gas sensor also includes an electrolyte in the first chamber. The gas sensor further includes a gas inlet and an integrated device die. The gas inlet is configured to provide fluid communication between the second chamber and the outside environs. The gas inlet is configured to permit gas to enter the second chamber from the outside environs. The integrated device die is mounted to the housing. The integrated device die comprises a sensor portion having a sensing element that is configured to detect the gas. The sensor portion of the integrated device die has a first side that is at least partially exposed to the first chamber and a second side that is at least partially exposed to the second chamber. The first side is opposite the second side.

In one embodiment, the sensing element comprises at least one of platinum black, ruthenium black, iridium black, carbon, and gold.

In one embodiment, the sensing element is at least partially disposed in the second chamber.

In one embodiment, the package further comprises one or more filters provided over the gas inlet.

In one embodiment, the package further comprises a die cap mounted to the integrated device die. The die cap at least partially defines the first chamber.

In one embodiment, the electrolyte comprises sulfuric acid or a solid electrolyte.

In one embodiment, the integrated device die is partially embedded in a molding compound. The gas inlet can be at least partially defined through an aperture of the molding compound.

In one embodiment, the integrated device die at least partially seals the first chamber from the second chamber.

In one embodiment, the package further comprises a package substrate. The integrated device die is mounted over the package substrate. The package substrate can comprise an opening. The second chamber can comprise the opening. The package can further comprise a standoff structure that vertically offsets the integrated device die from the package substrate. The standoff structure can comprises lateral channels that provides fluid communication between the second chamber and an outer chamber defined by the housing. The second chamber can disposed between the integrated device die and the package substrate. The first chamber can be disposed between the integrated device die and the package substrate. The package can further comprise an additional integrated device die that is mounted to the package substrate and overmolded with a molding compound. The integrated device die can be mounted to a die shelf that is defined by the molding compound over the additional integrated device die. The second chamber can be disposed between the integrated device die and the die shelf, The additional integrated device die can be laterally offset from the integrated device die.

In one embodiment, the integrated device die comprises a plurality of channels extending from the first side of the integrated device die to the second side of the integrated device die.

In one embodiment, the package comprises a package substrate and a package lid mounted to the package substrate. The second chamber can be defined at least in part by the package substrate and the package lid. The second chamber can be defined at least in part between the package substrate and the integrated device die.

In one embodiment, the second chamber comprises a lateral channel.

In one embodiment, the integrated device die comprises a processor portion, the processor portion integrated with the sensor portion.

In one aspect, a gas sensor package is disclosed. The gas sensor package includes a housing defining a first chamber and an electrolyte in the first chamber. The gas sensor package also includes a gas inlet that is configured to permit gas to enter the gas sensor package from outside environs. The gas sensor package further includes an integrated device die that is mounted to the housing. The integrated device die comprises one or more gas channels and a sensor portion that is disposed proximate to, and in fluid communication with, the one or more gas channels. The integrated device die has a sensing element that is configured to detect the gas. The sensor portion of the integrated device die has a first side that is at least partially exposed to the first chamber and a second side that is opposite the first side. The gas passes through the one or more gas channels to impinge upon the sensing element.

In one embodiment, the housing further defines a second chamber. The second side of the sensor portion can be at least partially exposed to the second chamber.

In one embodiment, the package further comprises one or more filters between the gas inlet and the sensor portion in a pathway of the gas.

In one aspect, a gas sensor package is disclosed. The gas sensor package includes housing means for defining a first chamber. The housing means has a gas inlet. The gas sensor package also includes an electrolyte in the first chamber. The gas sensor package further includes an integrated device die that is mounted to the housing means. The integrated device die comprises a sensor portion that has a sensing element that is configured to detect gas. The sensing element has a first side that is at least partially exposed to the first chamber and a second side that is opposite the first side.

In one embodiment, the housing means further defines a second chamber.

BRIEF DESCRIPTION OF THE DRAWINGS

Embodiments will now be described with reference to the following drawings, which are provided by way of example, and not limitation.

DETAILED DESCRIPTION

Various embodiments disclosed herein relate to gas sensor packages. For example, the gas sensor packages disclosed herein can enable sensing devices that are smaller and less expensive than conventional sensors. In various embodiments, the gas sensor packages can comprise a housing defining a first chamber and a second chamber. An electrolyte can be provided in the first chamber. A gas inlet can provide fluid communication between the second chamber and the outside environs. The gas inlet can be configured to permit gas to enter the second chamber from the outside environs. An integrated device die can be mounted to the housing. The integrated device die can comprise an amperometric sensor. The integrated device die can comprise a sensing element configured to detect the gas. The integrated device die can have a first side exposed to the first chamber and a second side exposed to the second chamber. The first side can be opposite the second side.

Figure 1:
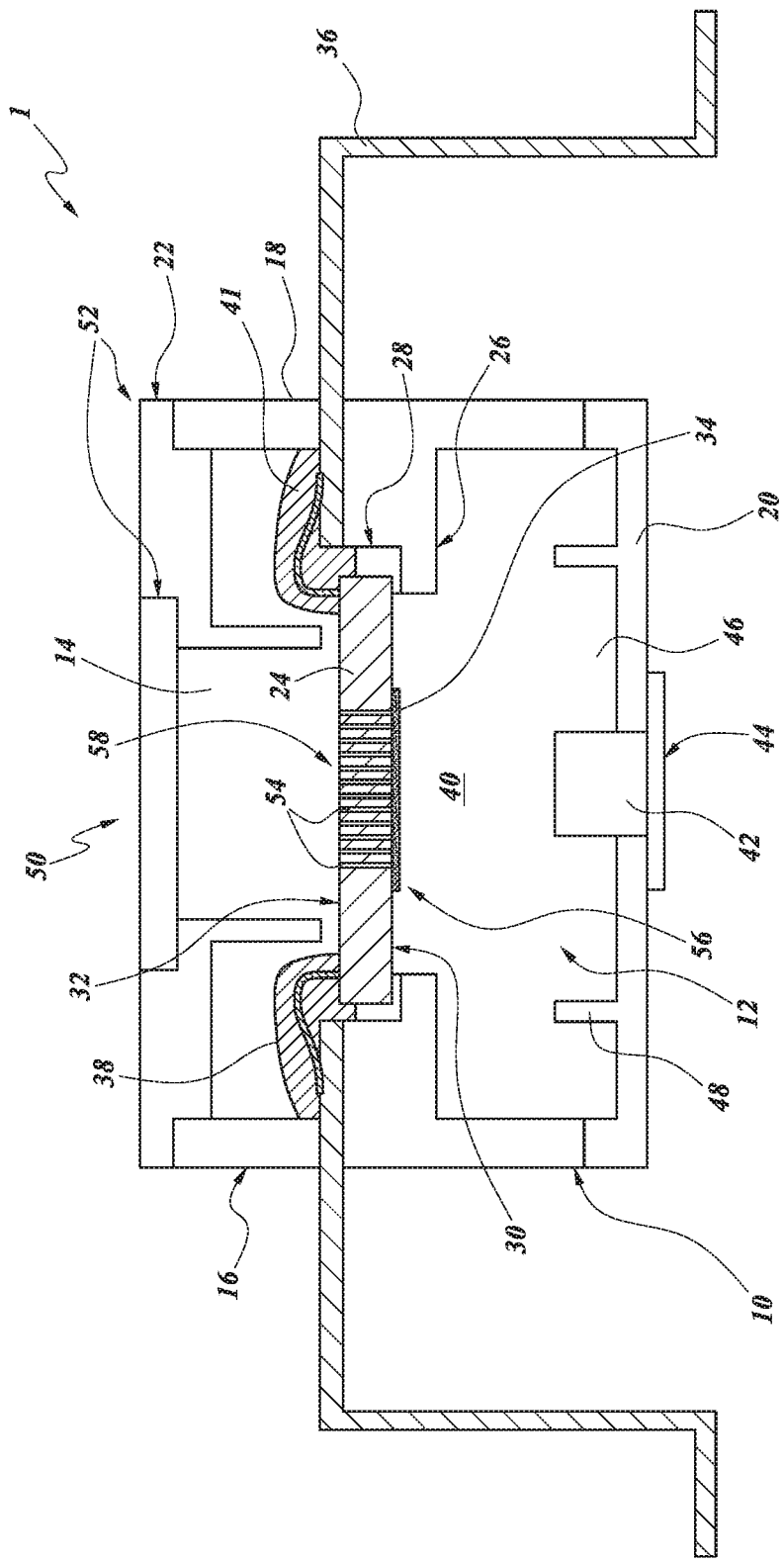
FIG. 1 is a schematic side sectional view of a gas sensor package having a package body at least partially defining first and second chambers, and a first lid and a second lid, according to one embodiment.

FIG. 1 is a schematic side sectional view of a gas sensor package 1, according to one embodiment. The gas sensor package 1 can include a housing 10 comprising first and second chambers 12, 14, as shown in FIG. 1. The housing 10 can be defined by a molded package body 16 that at least partially delimits the first and/or second chambers 12, 14. For example, as shown in FIG. 1, the package body 16 can comprise a nonconductive molding compound 18. As shown in FIG. 1, the package body 16 can comprise a dual-sided construction. A first lid 20 can be attached (e.g., by way of thermoplastic welding or joining techniques such as thermocompression bonding) to the package body 16 to partially define the first chamber 12. A second lid 22 can be attached (e.g., by way of thermoplastic welding or joining techniques such as thermocompression bonding) to the package body 16 to partially define the second chamber 14.

An integrated device die 24 can be physically mounted to a ledge 26 defined in the package body 16. The die 24 can be disposed between the first and second chambers 12, 14. A die attach or sealant compound 28 can mechanically attach the die 24 to the ledge 26. The integrated device die 24 can comprise an amperometric sensor. The integrated device die 24 can comprise a sensing element 34 on a first side 30 of the die 24. For example, the sensing element 34 can be adhered or laminated to the die 24. In various embodiments, the sensing element 34 can comprise platinum black or other types of electrodes used in electrochemical applications. In some embodiments, the sensing element 34 can comprise ruthenium black, iridium black, carbon, gold black, or gold. For example, in various embodiments, platinum black can be used for sensing carbon monoxide and hydrocarbons, such as alcohol, etc. In various embodiments, sintered platinum or iridium can be used for sensing hydrogen gas. Gold black may be used to detect sulfur containing compounds, such as hydrogen sulfide. In some embodiments, stabilized iridium may be used to detect gases such as ammonia and hydrazine.

In some embodiments, the sensing element 34 can electrically connect to corresponding contact pads (not shown) on the die 24. In other embodiments, the sensing element 34 can be formed as part of the die 24. In various embodiments, the sensing element 34 can be printed on a sensor part of the die 24 over capillaries or channels. In some embodiments, a cap can be attached over the sensing element 34, for example, to protect the sensing element 34. Furthermore, the die 24 can comprise other active circuitry and electrical interconnects connecting the active circuitry to the sensing element 34 for preprocessing signals detected by the sensing element, in some embodiments. As shown in FIG. 1, contact pads on a second side 32 of the die 24 can electrically connect the active circuitry or the interconnects to leads 36 of the package 1, e.g., by way of wire bonds 38. The wire bonds 38 may comprise gold or aluminum bonding wires, and may be bonded to the pads of the die 24 at room temperature to ensure that temperature limits of the sensing element are not exceeded. An encapsulant 41 or glob-top can be applied over the wire bonds 38 to protect the wire bonds 38 and/or electrically isolate the wire bonds 38. In other embodiments, the die 24 can be flip chip mounted to a substrate or package body, e.g., by way of solder balls or anisotropic conductive film (ACF), but such an arrangement may introduce additional costs as compared with wire bonding.

As shown in FIG. 1, an electrolyte 40 can be provided in the first chamber 12 of the package 1. The electrolyte 40 can comprise any suitable type of electrolyte for gas sensing applications, including, e.g., acids, such as a solution comprising sulfuric acid (e.g., a 40% sulfuric acid solution), bases, salts, organic electrolytes, gel electrolytes, polymer electrolytes, etc. In other embodiments, the electrolyte 40 can comprise other types of liquids (including gels) or solid electrolytes. In various embodiments, a combination of liquid and solid can be used for the electrolyte 40, such as water and a conductive polymer, for example, a sulfonated tetrafluoroethylene based fluoropolymer-copolymer (e.g., Nafion® manufactured by DuPont USA). For example, in some embodiments, the first lid 20 can be attached to a lower portion of the package body 16 as explained above. The electrolyte 40 can be flowed into the first chamber 12 by way of an opening 42. A sealing cap 44 can be provided over the opening 42 to seal the electrolyte 40 in the first chamber 12. In FIG. 1, the sensing element 34 can be exposed to the electrolyte 40 (for example, contacting the electrolyte) and/or at least partially disposed in the first chamber 12.

The first chamber 12 can also include a wicking material 46 to ensure that the electrolyte 40 contacts the sensing element 34. The wicking material 46 can comprise any suitable type of material, including, for example, a glass fiber matting in the first chamber 12. In various embodiments, the wicking material 46 can comprise a discrete component that is provided in the first chamber 12. In some embodiments, the wicking material 46 may comprise an open-cell foam that can be dispensed in fluid form to fill the first chamber 12. For example, projections 48 shown in FIG. 1 can cooperate with the wicking material 46 to press or draw the electrolyte 40 upwards to maintain contact with the sensing element 34. In the absence of the wicking material 46, there may be an air gap below the sensing element 34 such that the electrolyte 40 does not contact the sensing element 34 along its area. The wicking material 46 may also prevent splashing of the electrolyte 40 during dispensing and capping of the sealing cap 42. Thus, providing the wicking material 46 can improve the sensing capabilities of the gas sensor package 1 by maintaining contact between the electrolyte 40 and the sensing element 34.

The second chamber 14 can fluidly communicate with the outside environs by way of a gas inlet 50. As shown in FIG. 1, one or more filters 52 can be provided across the gas inlet 50. The filter(s) 52 can comprise mechanical barriers configured to prevent debris from entering the second chamber 14. In some embodiments, the filter(s) 52 can additionally or alternatively be configured to filter out organic compounds or other undesirable contaminants. Two filters 52 are illustrated in FIG. 1, but any suitable number and type of filters can be provided across the gas inlet 50 between the second chamber 12 and the outside environs. The filter(s) 52 may be provided before or after the second lid 22 is attached to the package body 16. The filter(s) 52 may be any suitable type of filter, such as a graphite filter, a polytetrafluoroethylene (PTFE) anticondensation filter or dust filter.

During operation, gas(es) can enter the second chamber by way of the gas inlet 50 and the filter(s) 52. As shown in FIG. 1, the second side 32 of the die 24 is exposed to the second chamber 14 and to the gas(es) entering the second chamber 14. The die 24 can comprise one or a plurality of channels 54 or capillaries formed through the die 24, e.g., from the second side 32 of the die 24 exposed to the second chamber 14 to the first side 30 of the die 24 on which the sensing element 34 is mounted or otherwise disposed. As shown in FIG. 1, the sensing element 34 can be disposed on a portion of the first side 30 of the die 24, and another portion of the first side 30 of the die 24 can be exposed to the electrolyte 40 in the first chamber 12. The die 24, therefore, can comprise a material resistant to the electrolyte 40 (e.g., an acid) such that the electrolyte 40 does not damage the die 24. Thus, the first side 30 of the die 24 can comprise a "wet" side 56 of the die 24, and the second side 32 of the die 24 can comprise a "dry" side 58 of the die 24. In various embodiments, the die 24 can comprise a semiconductor material such as silicon. Importantly, the die attach material or sealant, in cooperation with the integrated device die 24, can seal and/or fluidly separate the first chamber 12 from the second chamber 14 such that the electrolyte 40 does not enter the second chamber 14 from the first chamber 12. The die 24 can act as a barrier between the electrolyte 40 in the first chamber 12 and the gas(es) in the second chamber 14.

Gas passing through the channels 54 can contact the dry side 58 of the sensing element 34 on an opposite side of the wet side 56 of the sensing element 34, which contacts the electrolyte 40. In some embodiments, the gas can diffuse into the sensing element 34 of the integrated device die 24 (e.g., amperometric sensor die) and the integrated device die 24 can generate current, for example, as a consequence of chemical reactions of the gas at an interface between the sensing electrode 34 and the electrolyte 40 in the first chamber 12. A magnitude of the generated current is proportional to a gas concentration near the sensing element 34. Beneficially, the embodiment of FIG. 1 can enable the production of smaller-scale gas sensor packages that are simple and less expensive as compared with conventional gas sensors.

In some embodiments, the die 24 can include through substrate vias (TSVs) from the first side 30 of the die 24 that receives the sensing element 34 to the second side 32 opposite the first side 30, as illustrated, for example, in FIGS. 6 and 9-11. The TSVs on the second side can be connected to the wire bonds 38 to make electrical connection with the leads 36.

Figure 2:
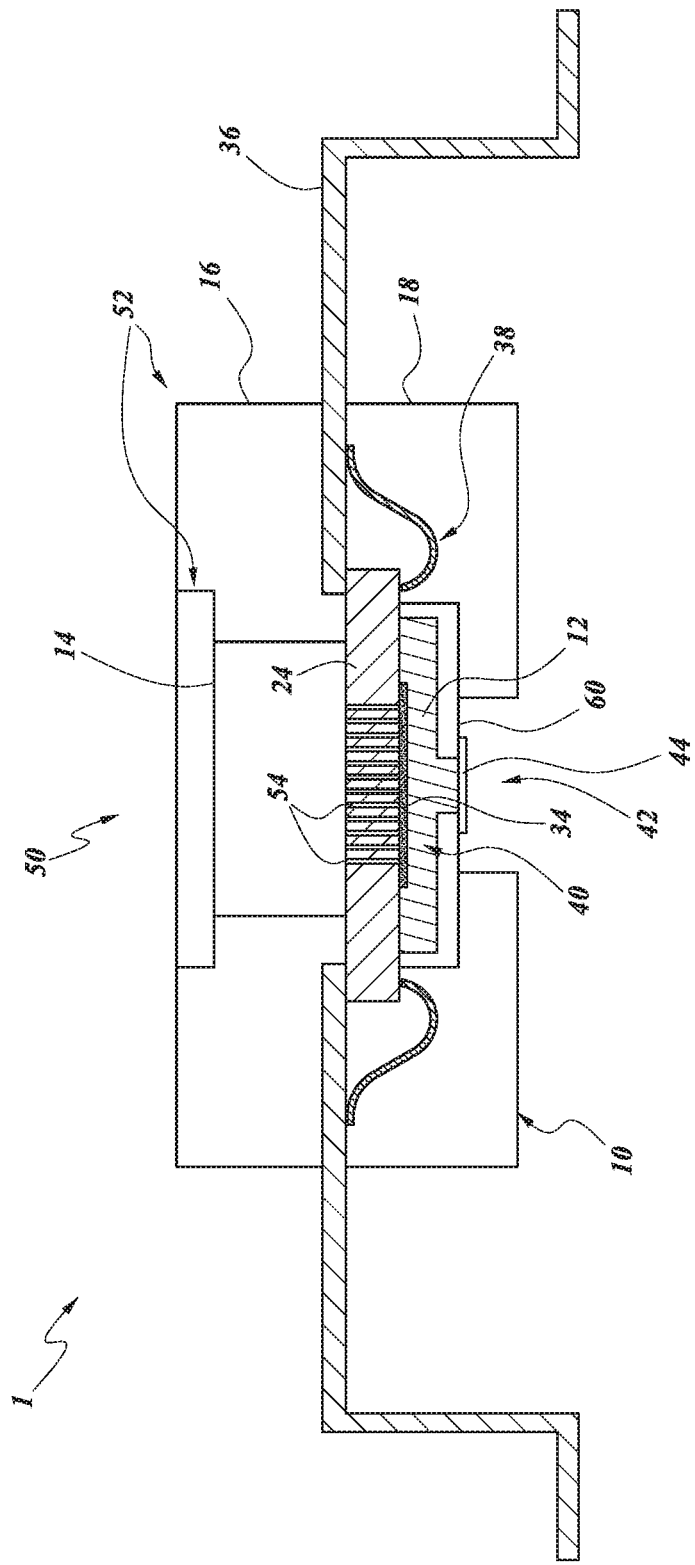
FIG. 2 is a schematic side cross-sectional view of a gas sensor package having a die cap at least defining a first chamber, according to another embodiment.

FIG. 2 is a schematic side cross-sectional view of a gas sensor package 1, according to another embodiment. Unless otherwise noted, the components of FIG. 2 may be the same as or generally similar to like-referenced components of FIG. 1. Further, the package 1 may operate generally similar to the package 1 of FIG. 1, in that gas can enter the gas inlet 50 and pass from the second chamber 14 and through the channels 54 to the first chamber 12. Current generated by the sensor die 24 can be measured, and the measured current can be representative of one or more target gas species. For example, as with FIG. 1, the gas sensor package 1 can comprise a first chamber 12 in which an electrolyte 40 is disposed and a second chamber 14 that fluidly communicates with the outside environs by way of a gas inlet 50 and one or more filters 52 disposed over the gas inlet 50. Additionally, unlike the embodiment of FIG. 1, in which the package body 16 and a package lid 20 define the first chamber 12, in the embodiment of FIG. 2, a die cap 60 can be attached to or formed with the integrated device die 24. The die cap 60 can define a smaller first chamber 12 than in the embodiment of FIG. 1, which can beneficially enable a smaller gas sensor package.

In the embodiment of FIG. 2, moreover, the package body 16 can be molded about the illustrated components by way of film assist molding (FAM), which combines high volume molding processes with the ability to leave an opening 42 such as that shown in FIG. 2. For example, in some embodiments, the integrated device die 24, the die cap 60, and the leads 36 can be molded using FAM, and the opening 42 may be left open by providing a tip or insert on the bottom of the die cap 60 such that the opening 42 is not molded. After molding, the electrolyte 40 (e.g., sulfuric acid) can flow through the opening 42 and into the first chamber 12. The sealing cap 44 (or a sealant or adhesive) can be provided over the opening in the die cap 60 to seal the electrolyte 40 in the first chamber 12, e.g., by way of a suitable sealant or adhesive. Beneficially, therefore, the gas sensor package 1 of FIG. 2 can utilize low cost molding techniques and materials at any suitable temperature, since the electrolyte 40 can be provided after molding, but assembly is simplified by omitting separate lid attachment for the first chamber 12. Moreover, the die 24 can be supported by, and at least partially embedded in, the package body 16 which may be defined by the molding compound 18. There may be no separate die paddle in various embodiments. For example, as shown in FIG. 2, the die 24 may be supported by the package body 16 and distal portions of the leads 36. The package body 16 can at least partially embed end portions of the die 24 so as to support the die 24. In some embodiments, the die 24 can be adhered to the distal portions of the leads 36. Further, as shown in FIG. 2, the molding compound 18 can be defined to include recesses for receiving the filter(s) 52. In some embodiments, the filter(s) 52 may be flush with or below the top surface of the package body 16. In some embodiments, one or more filter(s) 52 may protrude above the top surface of the package body 16.

Further, in embodiment of FIG. 2, electrical connections (e.g., the wire bonds 38) between the die 24 and the lead 36 may be covered with the molding compound 18 that at least partially defines the package body 16. Therefore, protection for the wire bonds 38 and/or electrical isolation of the wire bonds 38 may be provided without the separate encapsulant 41 or glob-top shown in FIG. 1.

Figure 3:
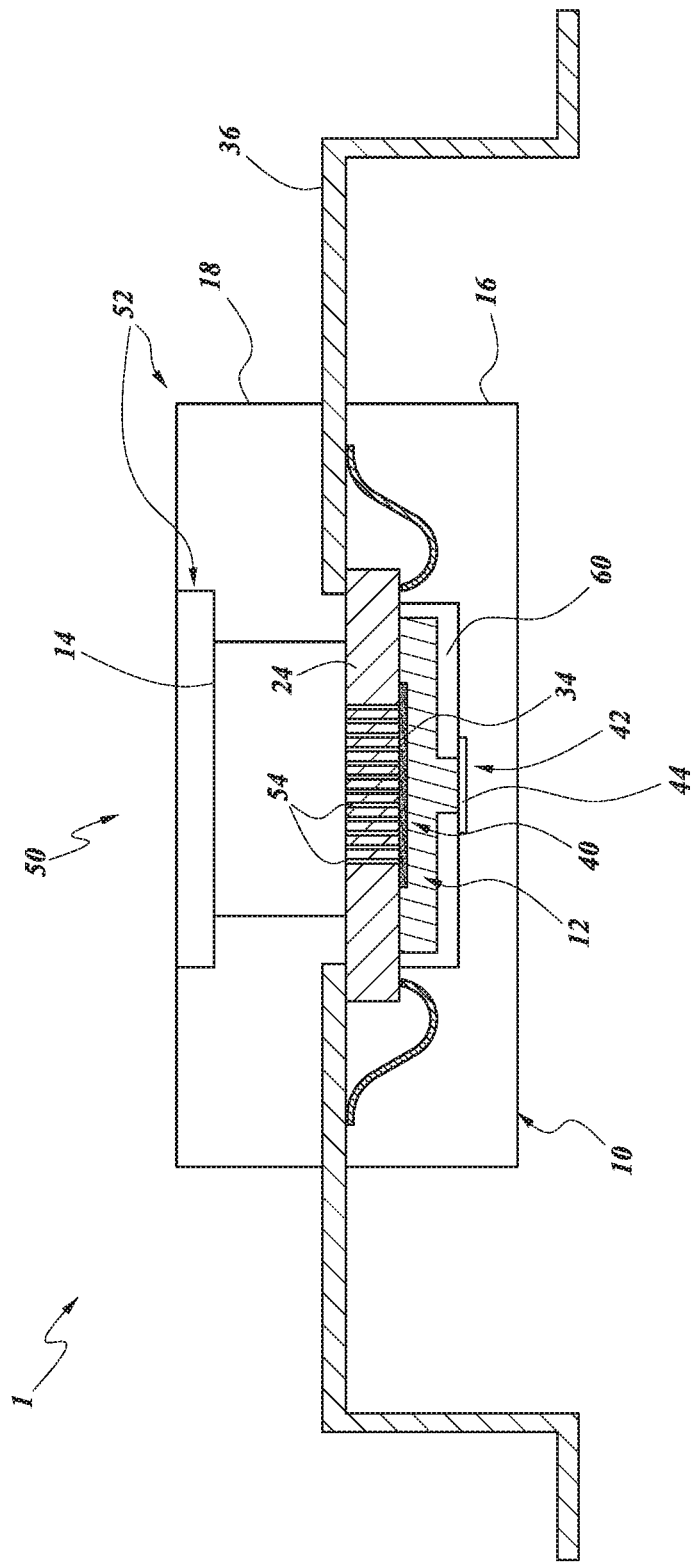
FIG. 3 is a schematic side cross-sectional view of a gas sensor package with a molding material provided over the die cap, according to another embodiment.

FIG. 3 is a schematic side cross-sectional view of a gas sensor package 1, according to another embodiment. Unless otherwise noted, the components of FIG. 3 may be the same as or generally similar to like-referenced components of FIGS. 1-2, and may operate or function in a generally similar manner. Unlike the embodiment of FIG. 2, in which the sealing cap 44 can be applied after filling the first chamber 12 with the electrolyte 40 either before or after molding, in FIG. 3, the electrolyte 40 can be provided in the first chamber 12 prior to the molding of the package body 16. For example, the first chamber 12 defined at least in part by the die cap 60 can be filled with the electrolyte 40 at the wafer level, and the sealing cap 44 can be applied over the opening 42 in the die cap 60. The molding compound 18 can be provided over the die cap 60 and the sealing cap 44 in FIG. 3. In some embodiments, therefore, the die cap 60, the electrolyte 40, and the sealing cap 44 can be applied to a wafer having multiple integrated device regions. The integrated device regions can be singulated to define a plurality of dies with the electrolyte 40 provided before singulation. In still other embodiments, the electrolyte 40 may be provided in the die cap 60 chamber after singulation of the wafer.

Figure 4:
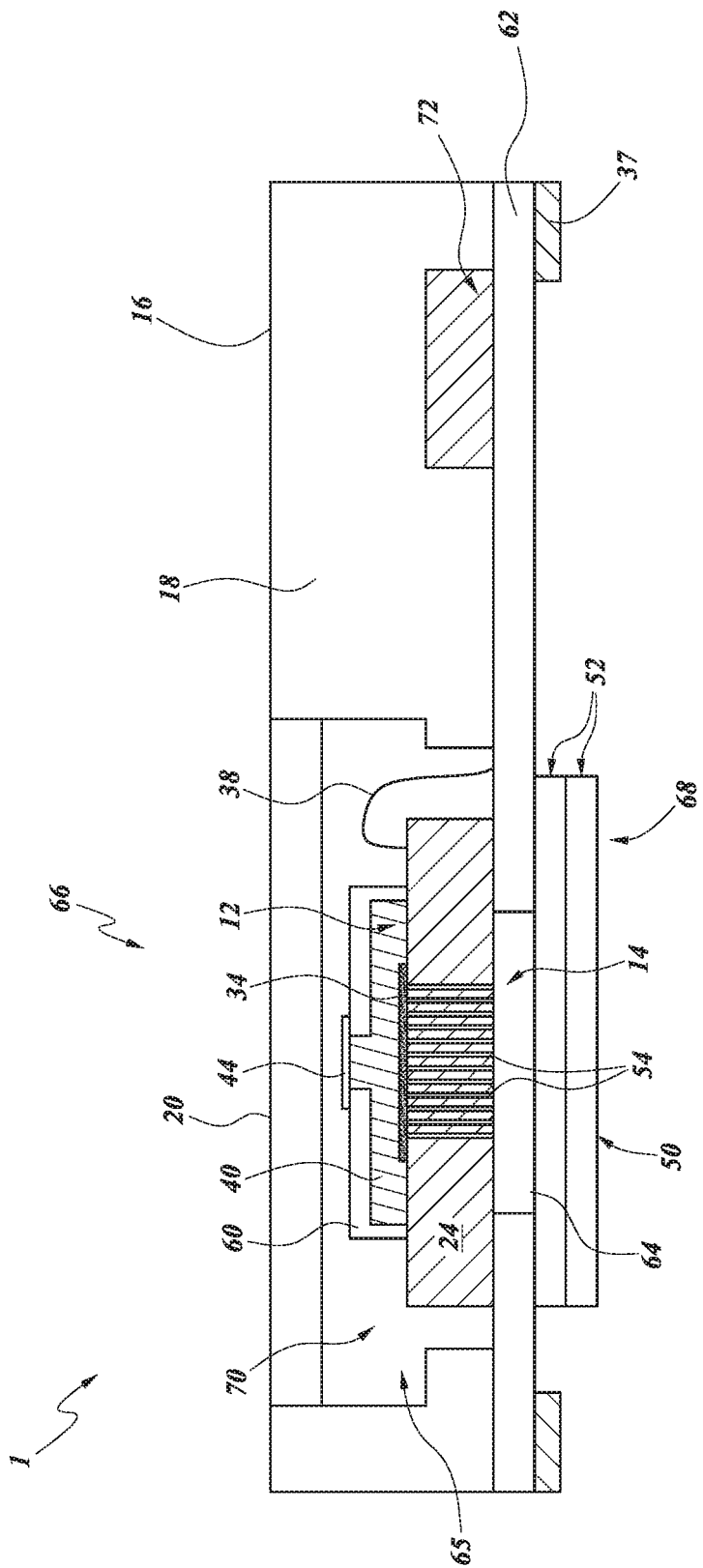
FIG. 4 is a schematic side cross-sectional view of a gas sensor package having a package substrate with a second integrated device die mounted to the package substrate, according to another embodiment.

FIG. 4 is a schematic side cross-sectional view of a gas sensor package 1, according to another embodiment. Unless otherwise noted, the components of FIG. 4 may be the same as or generally similar to like-referenced components of FIGS. 1-3, and may operate or function in a generally similar manner. For example, as with FIGS. 1-3, the package of FIG. 4 can comprise a first chamber 12 and a second chamber 14 on opposing sides of the integrated device die 24. Moreover, the package 1 can comprise a molded package body 16 (which may be formed by a FAM technique). The package body 16 can be applied over or coupled with a package substrate 62, which may comprise a laminate substrate such as a printed circuit board (PCB) substrate, a ceramic substrate, or any other suitable type of substrate. The package substrate 62 can comprise an opening 64 that can at least partially define the gas inlet 50. As shown in FIG. 4, the opening 64 and the gas inlet 50 can be disposed on a bottom side 68 of the gas sensor package 1. One or more filters 52 can be coupled to the package substrate 62 over the opening 64. The second chamber 14, which can be in fluid communication with gas(es) in the outside environs by way of the gas inlet 50, can be defined at least in part by the opening 64 in the package substrate 62. The integrated device die 24 can be disposed over the opening 64 and the second chamber 14.

A lid 20 can be coupled to or embedded within the package body 16. For example, as explained above, FAM techniques can enable the formation of openings or voids 65 in the molding compound 18 of the package body 16. The lid 20 can be connected to the package body 16 within openings or voids defined in the molding compound 18. The lid 20 and the package body 16 can define an outer chamber 70 in which the integrated device die 24 is disposed. The die cap 60 can be mounted to the integrated device die 24 over the sensing element 34 to define the first chamber 12 in which the electrolyte 40 is provided. In some embodiments, the die cap 60 can be pre-filled with the electrolyte 40, and the sealing cap 44 can seal the first chamber 12 of the die cap 60 during wafer-level assembly. In other embodiments, the first chamber 12 of the die cap 60 can be filled with electrolyte 40 during packaging, e.g., after the die 24 is mounted to the package substrate 62 but before application of the lid 20. As with the above embodiments, the integrated device die 24 and associated die attach materials or sealants can act as a barrier or seal between the electrolyte 40 in the first chamber and the gas(es) in the second chamber 14.

Further, as shown in FIG. 4, a second integrated device die 72 can be mounted to the package substrate 62 and can be laterally offset relative to the integrated device die 24 coupled with the sensing element 34. In FIG. 4, the second die 72 can be embedded in the molding compound of the package body 16, which can beneficially enable standard high temperature packaging and molding techniques. The device die 24 and sensing element 34 can be packaged in a separate, low temperature packaging stage so as to mitigate damage to the sensing element as a result of high temperature processing. The integrated device die 24 can be wire bonded to the substrate 62, and the second integrated device die 72 can electrically communicate with the integrated device die 24 by way of conductive traces embedded in or on the package substrate 62 (e.g., by way of flip-chip or wire bonding interconnections, which are not shown in FIG. 4). In various embodiments, the wire bonds 38 may be protected by a glob-top or molding material (see, for example, FIG. 1). In other embodiments, the wire bonds 38 may not be protected by a glob-top or molding material. In some embodiments, the second die 72 can process signals transduced by the integrated device die 24 with the sensing element 34. Other devices (e.g., passives) can be similarly mounted on the package substrate 62 (e.g., laminate substrate) and communicate with the integrated device (sensor) die 24 and/or the second integrated device die 72 through the the package substrate 62 (e.g., laminate substrate) or directly. The packaging substrate 62 includes leads 37 on the lower surface thereof to facilitate electrical connection to larger electronic systems, e.g., by way of a mother board, such as a printed circuit board, or PCB.

Figure 5:
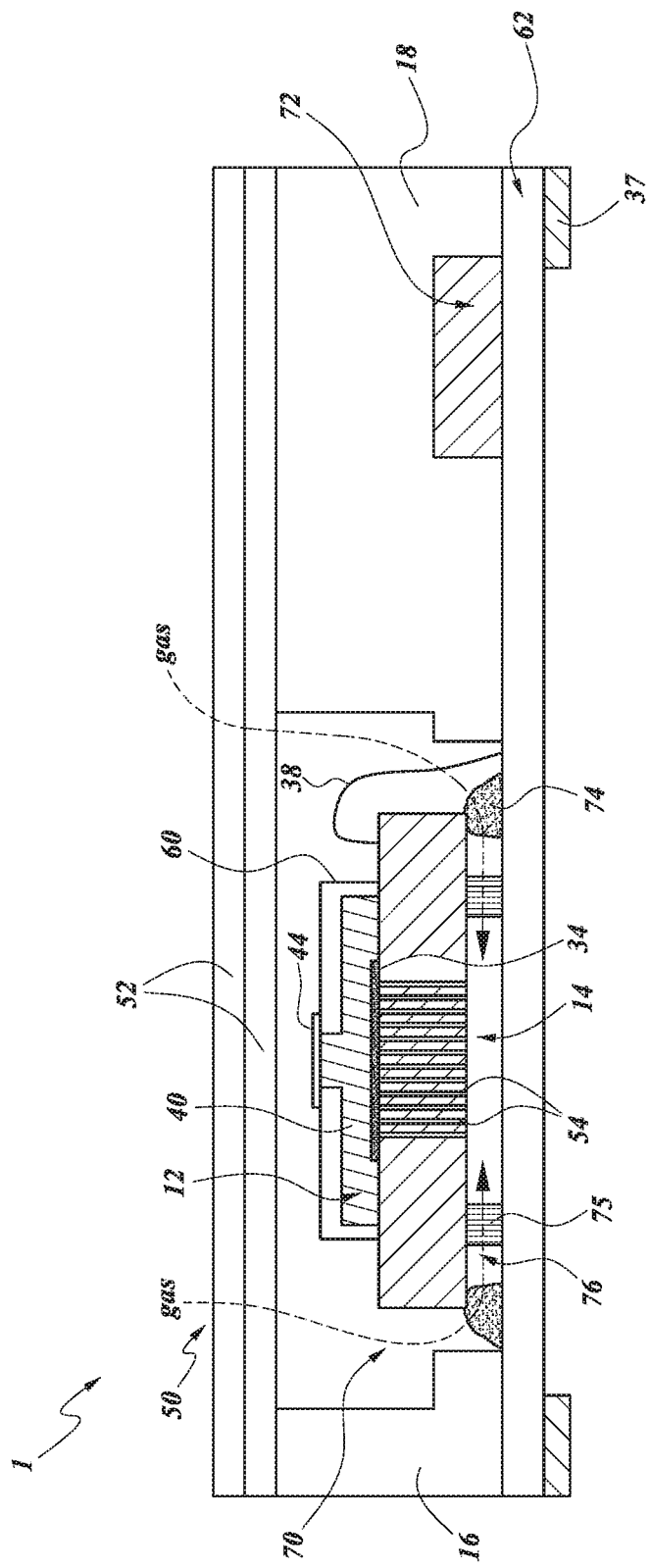
FIG. 5 is a schematic side cross-sectional view of a gas sensor package having first and second chambers in an outer chamber, according to another embodiment.

FIG. 5 is a schematic side cross-sectional view of a gas sensor package 1, according to another embodiment. Unless otherwise noted, the components of FIG. 5 may be the same as or generally similar to like-referenced components of FIGS. 1-4, and may otherwise operate or function in a generally similar manner. Unlike the embodiment of FIG. 4, for example, the gas inlet 50 can be provided at the top side of the package 1. The filter(s) 52 can be provided over an aperture defined in the molding compound 18 (e.g., which may be formed using a FAM technique) and over the gas inlet 50. As shown, the die 24 can be mounted to the package substrate 62 by way of a die attach material 74. Further, a standoff structure 75 can be provided to space the bottom surface of the die 24 vertically offset from the top surface of the package substrate 62. Gas can enter the outer chamber 70 of the package 1 through the gas inlet 50 and filters 52, and can pass laterally through lateral channels 76 to enter the second chamber 14. Thus, the standoff structure 75, the integrated device die 24, and the package substrate 62 can define the second chamber 14 in the embodiment of FIG. 5, which is in open fluid communication with the outer chamber 70. The lateral channels 76 within the standoff structure 75 can provide fluid communication between the outer chamber 70 and the second chamber 14. In various embodiments, the lateral channels 76 can be defined by etching laterally through the standoff structure 75 (which may comprise silicon). As with the embodiments described above, the die 24, the die cap 60 and the sealing cap 44 can define the first chamber 12 in which the electrolyte 40 is disposed. Thus, in FIG. 5, the second chamber 14 can be disposed between the die 24 and the package substrate 62. The first chamber 12 can be disposed between the die 24 and the gas inlet 50 or filters 52. In some embodiments the lateral channels 76 may comprise the second chamber 14.

Figure 6:
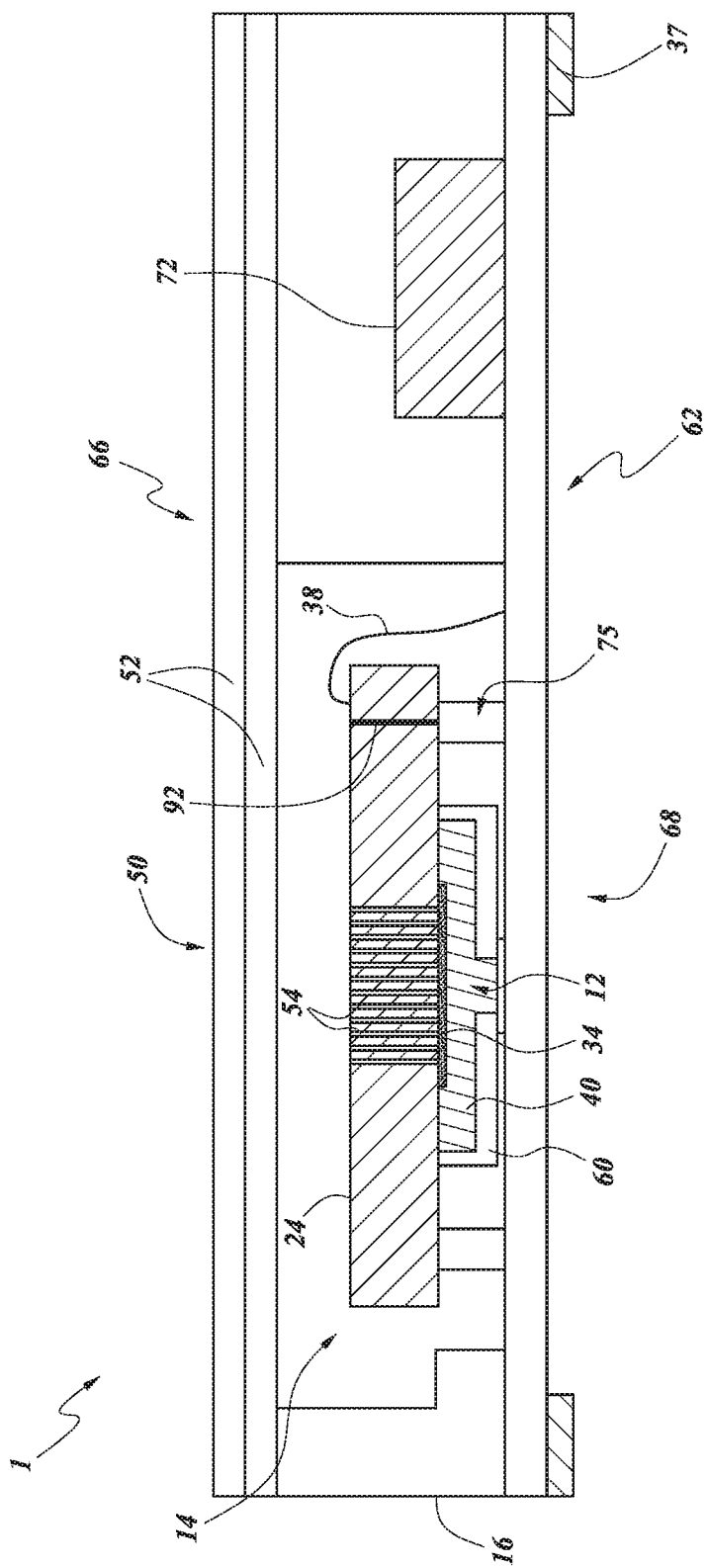
FIG. 6 is a schematic side cross-sectional view of a gas sensor package with a sensor die having a through substrate via, according to another embodiment.

FIG. 6 is a schematic side cross-sectional view of a gas sensor package 1, according to another embodiment. Unless otherwise noted, the components of FIG. 6 may be the same as or generally similar to like-referenced components of FIGS. 1-5, and may operate or function in a generally similar manner. As with the embodiment of FIG. 5, the gas inlet 50 and filter(s) 52 can be provided at a top side 66 of the package 1. Unlike the embodiment of FIG. 5, however, the outer chamber can directly serve as the second chamber 14, and the first chamber 12 can be disposed nearer the bottom side 68 of the package 1. One or more die supports 75 can support the die 24 above the package substrate 62 to improve the structural support of the die 24 during manufacturing and/or use, and to provide a space which can accommodate the thickness of the die cap 60 and first chamber 12. As shown in FIG. 6, the first chamber 12 can be disposed between the die 24 and the package substrate 62. As shown in FIG. 6, one or more through-silicon vias (TSVs) 92 can be provided to provide electrical communication between front and back surfaces of the die 24.

Figure 7:
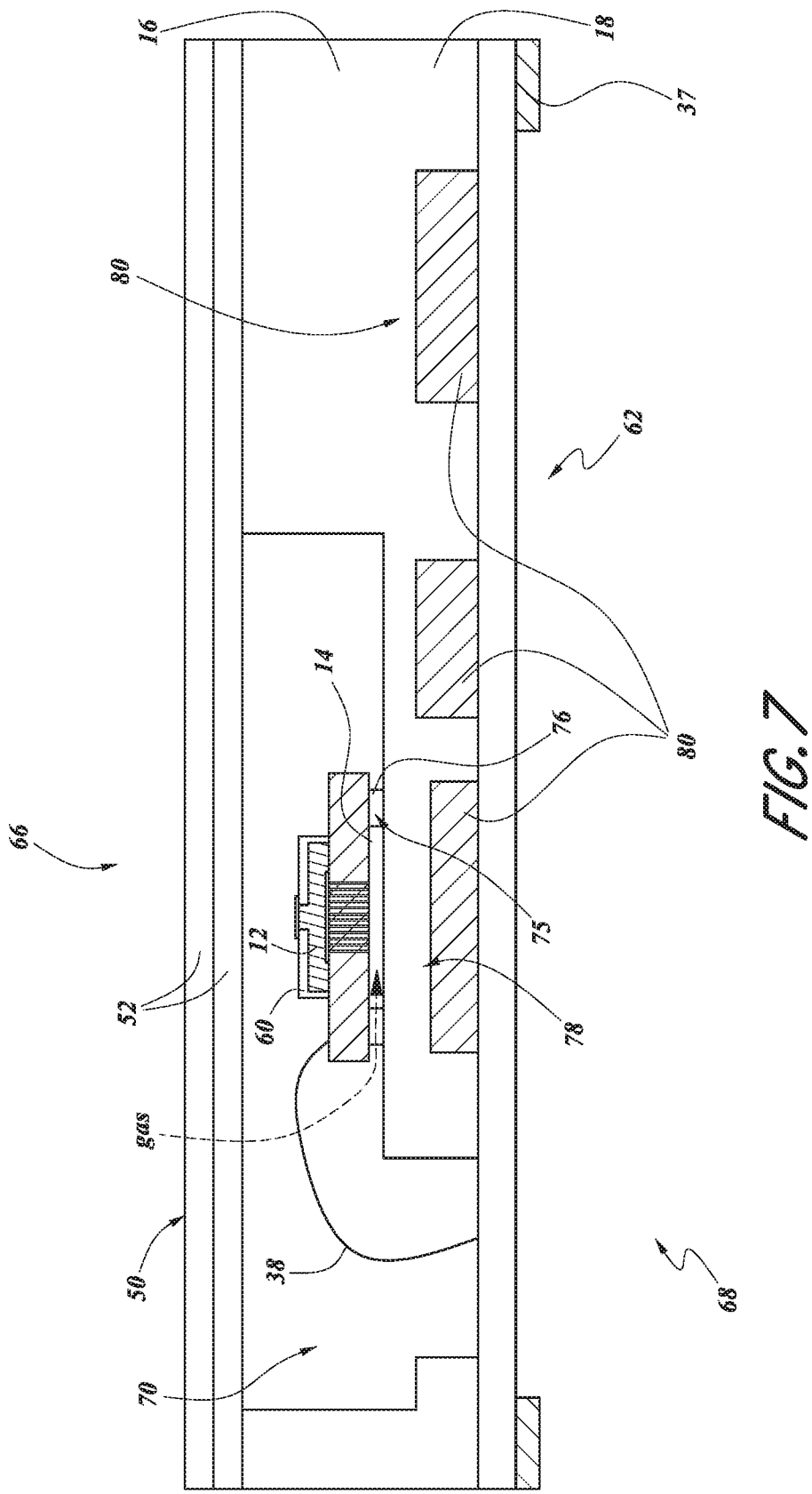
FIG. 7 is a schematic side cross-sectional view of a gas sensor package with a die shelf for the sensor die, according to another embodiment.

FIG. 7 is a schematic side cross-sectional view of a gas sensor package 1, according to another embodiment. Unless otherwise noted, the components of FIG. 7 may be the same as or generally similar to like-referenced components of FIGS. 1-6, and may operate or function in a generally similar manner. The package 1 of FIG. 7 may be similar to the package 1 shown in FIG. 5, e.g., the second chamber 14 may be disposed between the die 24 and the package substrate 62, or nearer the bottom side 68 of the package 1. The first chamber 12 and the electrolyte 40 may be disposed between the die 24 and the gas inlet 50, or nearer the top side 66 of the package 1. Unlike the embodiment of FIG. 5, however, in FIG. 7, the integrated device die 24 can be mounted over a die shelf 78 defined at least in part by the molding compound 18 of the package body 16. As shown in FIG. 7, the package body 16 can be overmolded over one or more additional integrated device dies and/or other electronic components 80 (e.g., passives) to define the die shelf 78. The integrated device die 24 with the sensing element 34 can be mounted to the die shelf 78 over the one or more additional devices or dies 80. The integrated device (sensor) die 24 can be electrically connected to the laminate package substrate 62, such as by way of the illustrated bond wires 38, for communication with the embedded dies and/or other electronic components 80.

As with FIG. 5, in FIG. 7, a standoff structure 75 can be provided to vertically offset the die 24 relative to the die shelf 78. Lateral channels 76 can be defined in the standoff structure 75 and/or the die shelf 78 during molding to enable fluid communication between the outer chamber 70 and the second chamber 14. Thus, gas(es) can enter the outer chamber 70 through the gas inlet 50 and filter(s) 52. The gas(es) can pass through the lateral channels 76 in the standoff structure 75 and/or the die shelf 78 to enter the second chamber 14. Beneficially, the embodiment of FIG. 7 can enable a lower package footprint since the integrated device die 24 can be stacked on the overmolded additional devices or dies 80.

Figure 8:
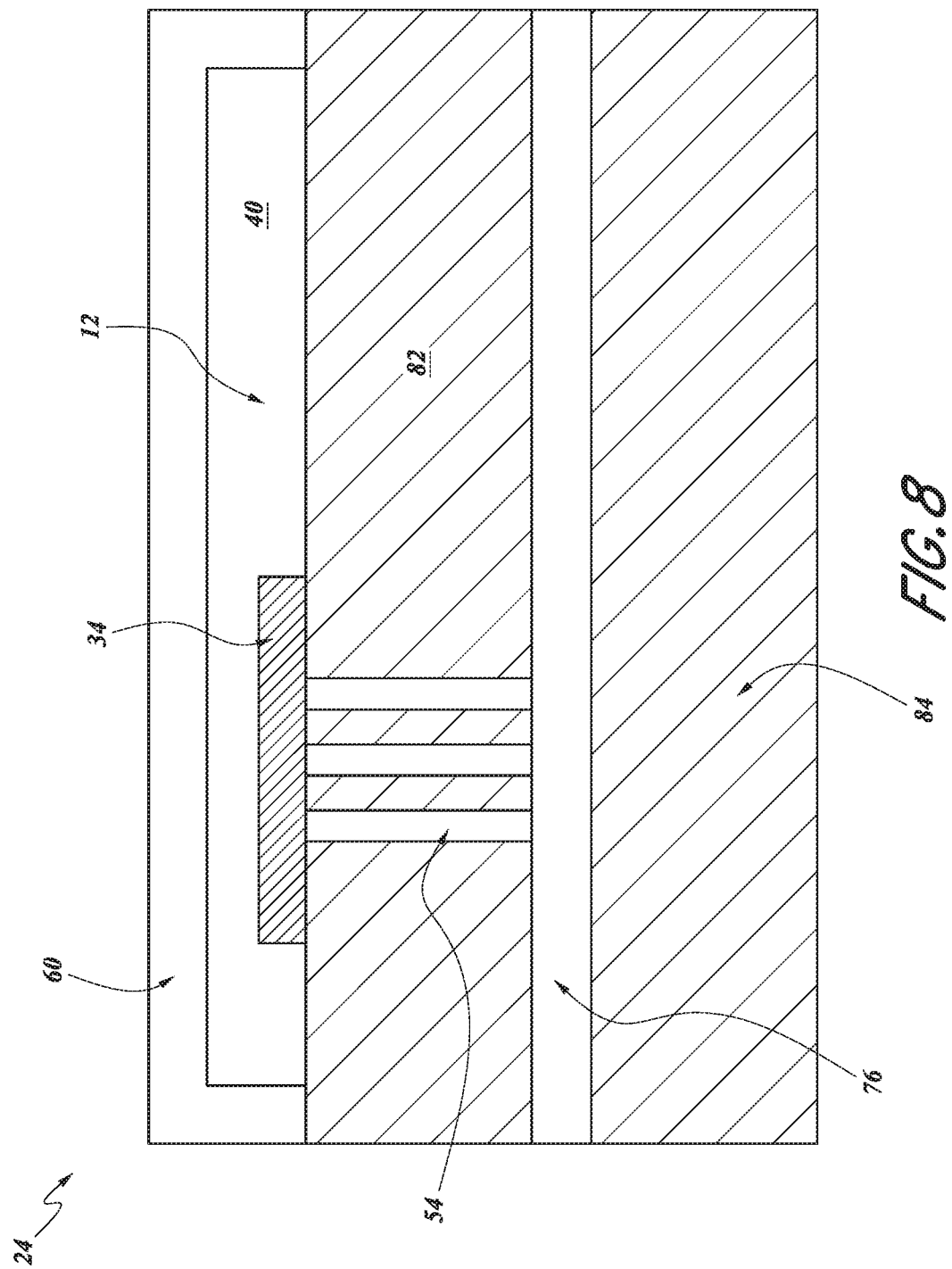
FIG. 8 is a schematic side sectional view of a sensor die in which a sensor portion and a processor portion are defined in a common unitary structure.

FIG. 8 is a schematic side sectional view of a sensor die 24 in which a sensor portion 82 and a processor portion 84 are defined in a common unitary structure. Unless otherwise noted, the components of FIG. 8 may be the same as or generally similar to like-referenced components of FIGS. 1-7. For example, as shown in FIG. 8, a sensing element 34 can be applied (e.g., printed or otherwise coupled) on the sensor portion 82 of the die 24 over the gas channels 54. An electrolyte 40 can be provided in the first chamber 12. The sensor die 24 of FIG. 8 can be used in conjunction with any of the packages disclosed herein. The sensor portion 82 and processor portion 84 can be made from the same substrate, e.g., the same wafer. For example, active processing circuitry can be defined in the processor portion 84, and additional routing circuitry can be defined in the sensor portion 82. A lateral chamber 76 or channel can be defined between the processor portion 84 and the sensor portion 82. The lateral chamber 76 or channel can provide a gas inlet for gas to enter the vertical channels 54 to interact with the sensing element 34. In some embodiments, the lateral chamber 76 can serve as the second chamber 14 to provide fluid communication to one side of the sensor portion of the die 24. In other embodiments, a chamber outside of the die 24 can serve as the second chamber 14.

In various embodiments, the lateral chamber 76 or channel can be defined by etching. For example, a sacrificial material can be deposited on the processor portion 84, and an etchant can be provided through the vertical channels 54 to etch the sacrificial material in the lateral chamber 76 or channel. The lateral channels 76 can be etched by wet etching, dry etching, or any other suitable method. In various embodiments, the sensor die 24 may comprise pre-formed channels, and the sensor die 24 and an application specific integrated circuit (ASIC) can be stacked together, e.g., by a die attach material. Additional details of the sensor die 24 shown in FIG. 8 may be found throughout U.S. Patent Publication No. US 2018-0059044, the entire contents of which are hereby incorporated by reference herein in their entirety and for all purposes.

Figure 9:
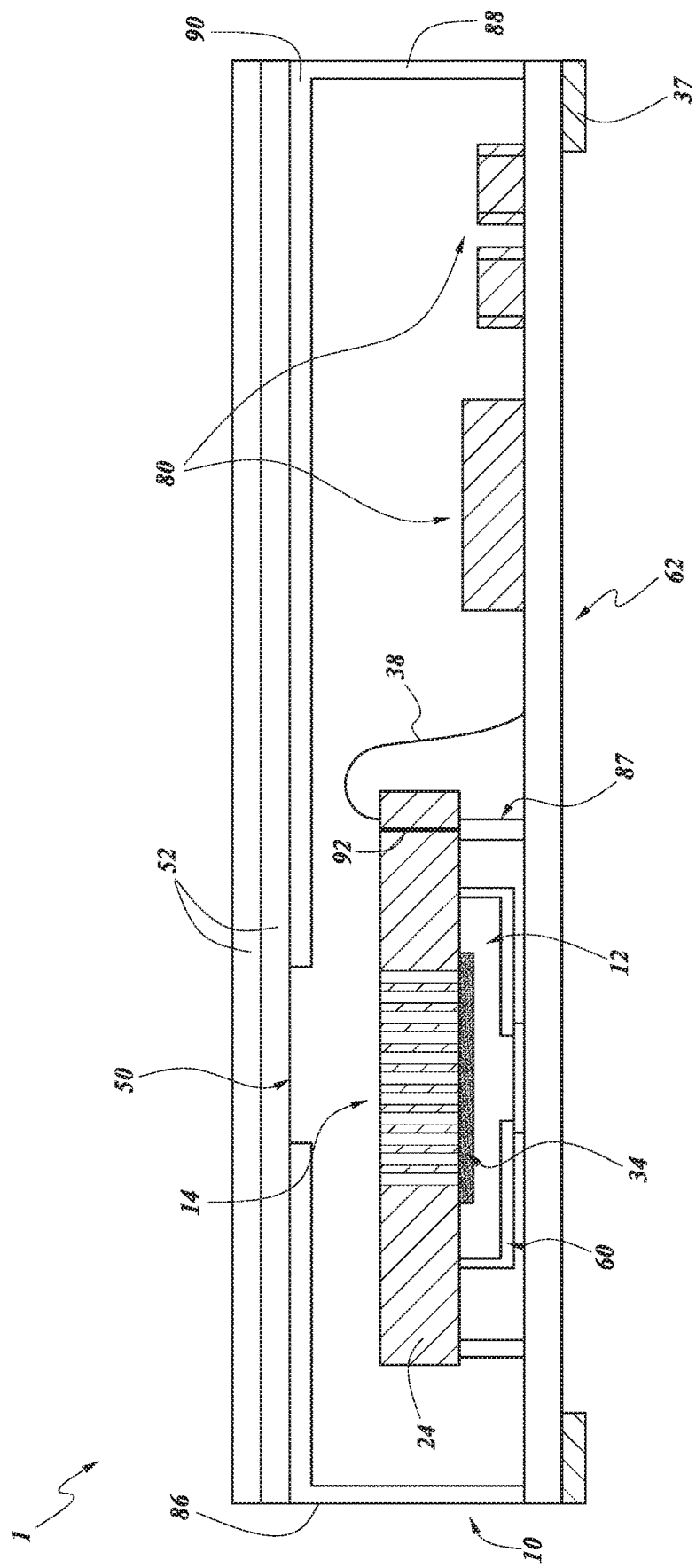
FIG. 9 is a schematic side cross-sectional view of a gas sensor package having a lid that defines a housing for the sensor die and other devices or dies, according to another embodiment.

FIG. 9 is a schematic side cross-sectional view of a gas sensor package 1, according to another embodiment. Unless otherwise noted, the components of FIG. 9 may be the same as or generally similar to like-referenced components of FIGS. 1-8, and may operate or function in a generally similar manner. In the embodiment of FIG. 9, the gas sensor package 1 can comprise a package lid 86 that at least partially defines the second chamber 14 that communicates with the gas inlet 50. As shown in FIG. 9, the sensor die 24 can be supported by a package substrate 62 (e.g., a laminate substrate) by way of intervening die supports 87 or dams. The die supports 87 or dams can comprise L- or T-shaped structures (e.g., molded dams) to restrict the bleed out of die attach material between the sensor die 24 and the package substrate 62, and to provide support to the die 24. However, it should be understood that the die supports 87 or dams can comprise other shapes suitable.

The package 1 can serve as a laminate-based system-in-package. As above, the electrolyte 40 can be provided in the first chamber 12 defined at least in part by the die cap 60. The sensor die 24 can be inverted in the illustrated embodiment, e.g., to reduce the distance between the gas inlet 50 and the sensor die 24 and sensing element 34. In the illustrated embodiment, the package lid 86 can be provided over the sensor die 24 and other dies, packages, and/or passive components 80. The package lid 86 can comprise a shaped lid, e.g., with one or more vertical legs 88 that support a horizontal upper lid portion 90. One or more filters 52 can be coupled to the lid 86. In FIG. 9, the filters 52 are disposed over the horizontal upper lid portion 90 of the package lid 86. However, in some embodiments, the filters 52 may be disposed inside the package lid 86 (e.g., under the lid portion 90), or both inside and outside of the package lid 86 (e.g., over and under the lid portion 90). The gas inlet 50 can comprise a port hole formed in the lid 86, e.g., the upper portion of the lid 86.

As explained above, the package lid 86 can at least partially define the second chamber 14. In the embodiment of FIG. 9, the sensor die 24 and other dies, packages, or passive components 80, including processor dies (e.g., ASICs) may also be disposed in the second chamber 14 defined at least in part by the lid 86. As explained above, the bonding wires electrically connecting the sensor die 24 or other dies, packages, or passive components 80 to the package substrate 62 may be protected by a polymer or glob-top. In other embodiments, the bonding wires may be exposed to the second chamber 14. In various embodiments, the filters 52 can be applied as sheets to the lid 86, and can protrude above the package body or housing 10. The filter(s) 52 can be applied to the lid 86 before or after attaching the lid 86 to the package substrate 62, according to various embodiments. In still other embodiments, the package lid 86 can comprise one or more recesses sized and shaped to receive and/or support the filter(s) 52. The filter(s) 52 can be compression fit and/or glued to the lid 86 to prevent gas leaks. In various embodiments, the filter(s) 52 can comprise a hydrophobic and/or dust film to reduce the risks of exposing the package 1 to moisture. Further, as shown in FIG. 9, one or more through-silicon vias (TSVs) 92 can be provided to provide electrical communication between front and back surfaces of the die 24.

Figure 10:
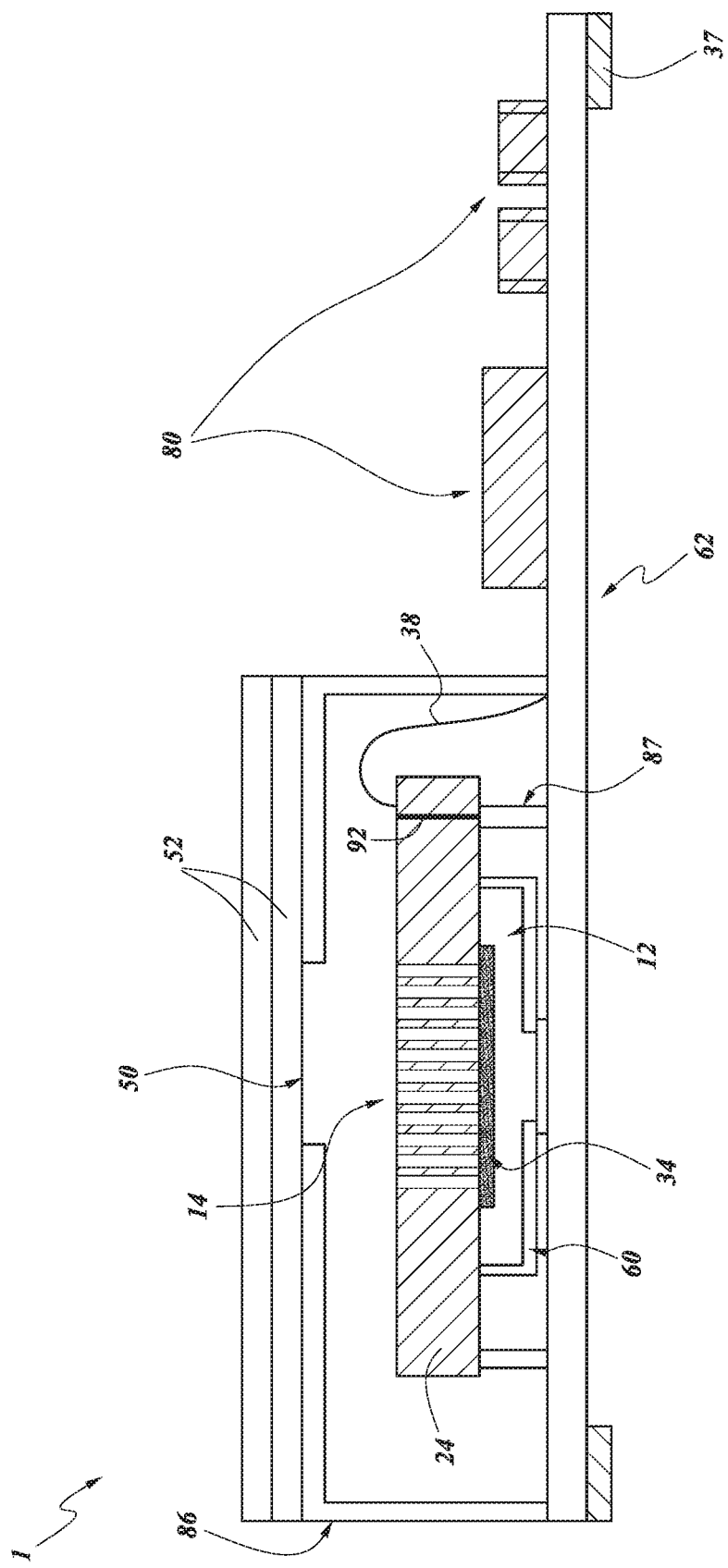
FIG. 10 is a schematic side cross-sectional view of a gas sensor package having other devices or dies outside of the housing defined by the lid, according to another embodiment.

FIG. 10 is a schematic side cross-sectional view of a gas sensor package 1, according to another embodiment. Unless otherwise noted, the components of FIG. 10 may be the same as or generally similar to like-referenced components of FIG. 9, and may operate or function in a generally similar manner. Unlike the embodiment of FIG. 9, however, in FIG. 10, the lid 86 may be disposed over the sensor die 24, but the other dies, packages, and/or passive components 80 may be mounted to the package substrate 62 and disposed outside the lid 86 and the second chamber 14.

Figure 11:
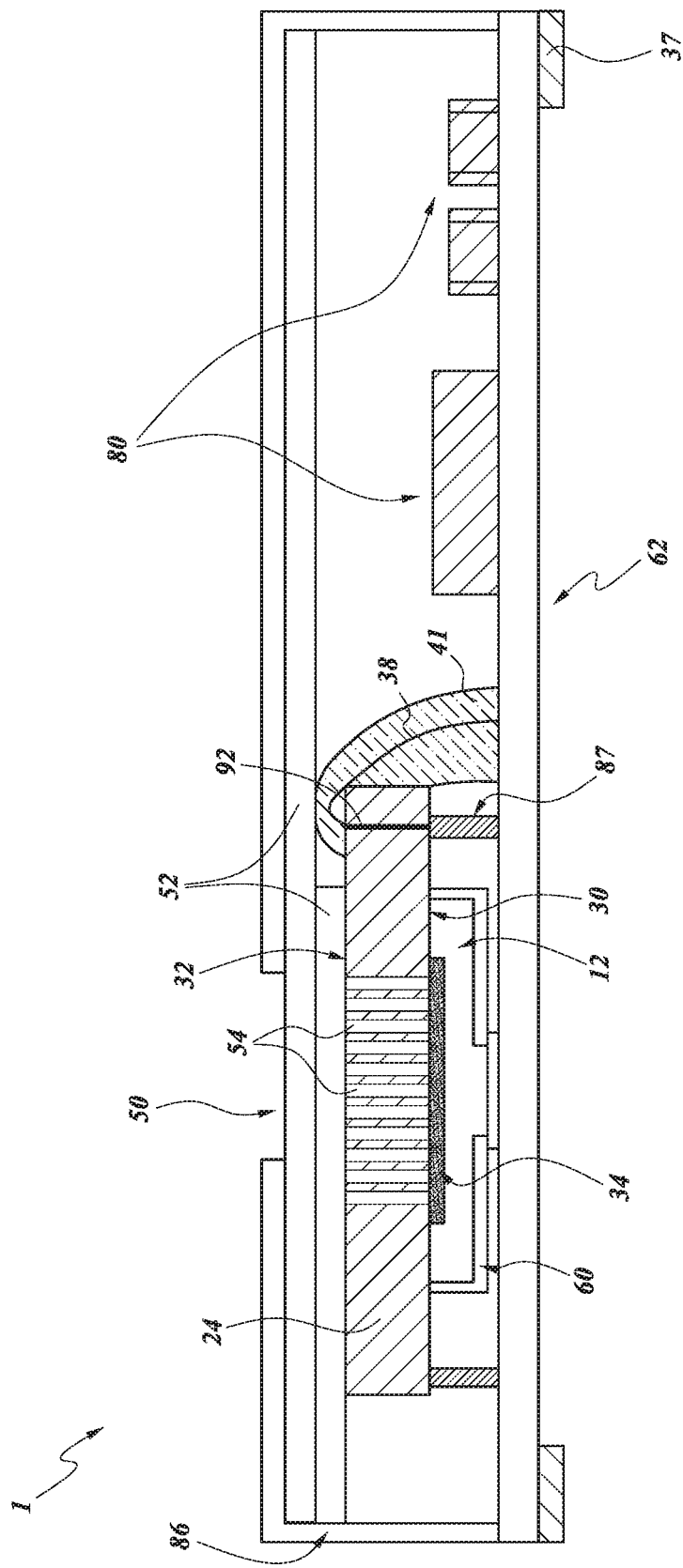
FIG. 11 is a schematic side cross-sectional view of a gas sensor package, according to another embodiment.

FIG. 11 is a schematic side cross-sectional view of a gas sensor package 1, according to another embodiment. Unless otherwise noted, the components of FIG. 11 may be the same as or generally similar to like-referenced components of FIGS. 9-10, and may operate or function in a generally similar manner. Unlike the embodiments of FIGS. 9-10, as shown in FIG. 11, the one or more filter(s) 52 can be provided on an inner surface of the lid 86, as opposed to on an outer surface of the lid (such as is shown in FIGS. 9-10). Furthermore, in the embodiment of FIG. 11, the filter(s) 52 may contact at least a portion the surface of the sensor die 24. In other embodiments, the lid 86 and filter(s) 52 may stand off from the sensor die 24, such that the second chamber 14 of the package 1 may also be defined by the lid 86 in a manner similar to that shown in FIGS. 9-10. The wire bond 38 can make electrical connection between the die 24 and the package substrate 62. In some other embodiments, the die supports 87 may make electrical connection between the sensor die 24 and the substrate 62. In the embodiment of FIG. 11, gas can pass through the gas inlet 50, through the gas channels 54, and into the first chamber 12. Current generated by the die 24 can be proportional to a gas concentration of the gas, which can be used to identify the gas.

Figure 12:
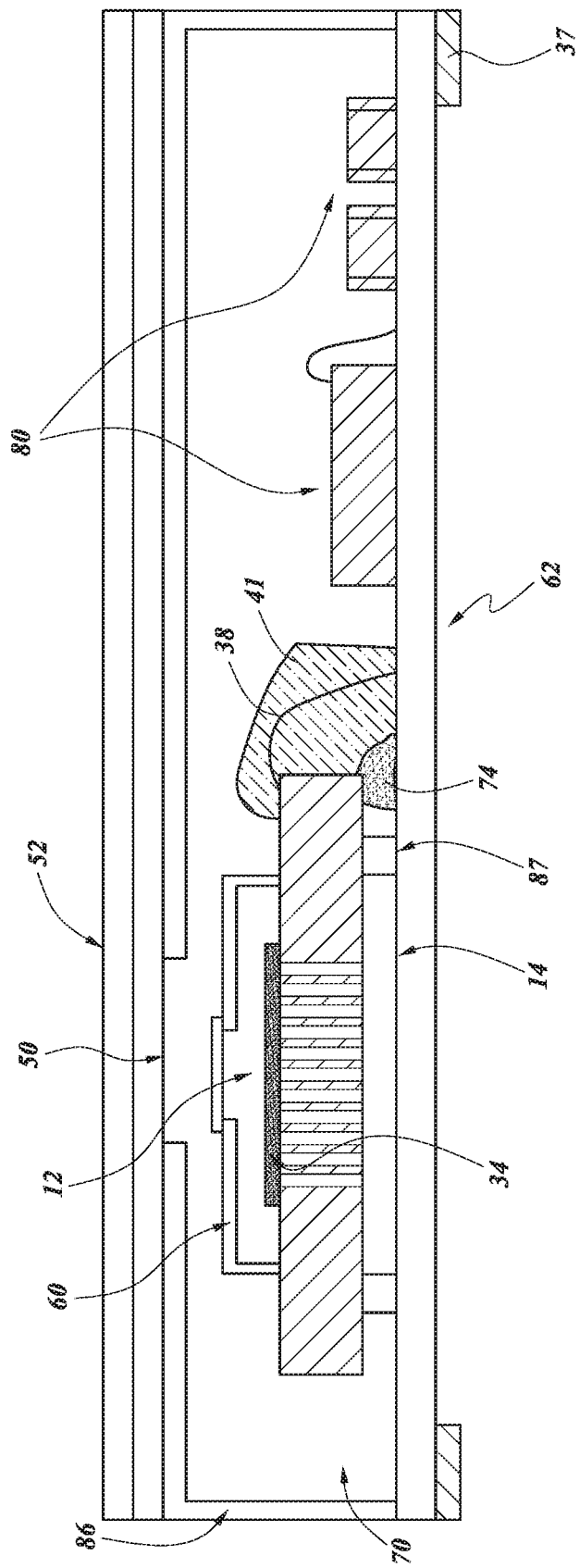
FIG. 12 is a schematic side cross-sectional view of a gas sensor package having a lid that defines the housing for the sensor die and other devices or dies, according to another embodiment.
Figure 13:
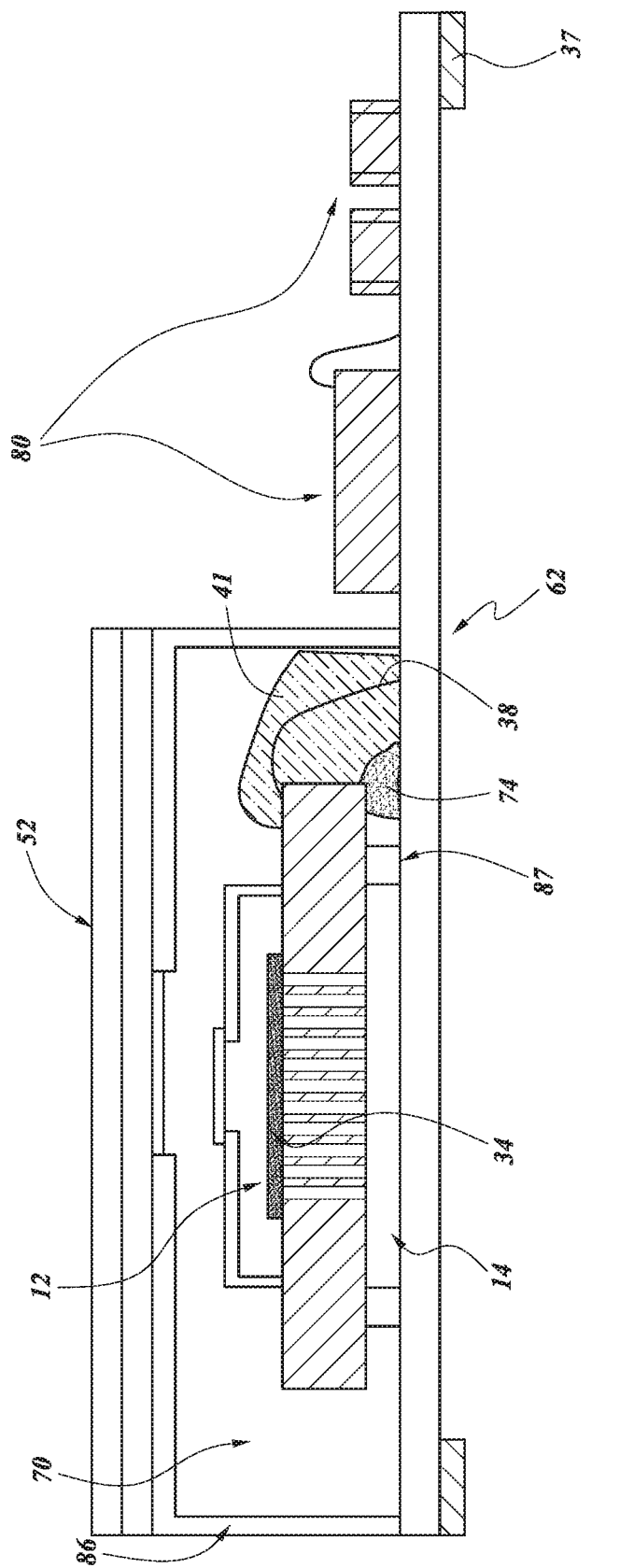
FIG. 13 is a schematic side cross-sectional view of a gas sensor package having other devices or dies outside of the housing defined by the lid, according to another embodiment.

FIG. 12 is a schematic side cross-sectional view of a gas sensor package 1, according to another embodiment. FIG. 13 is a schematic side cross-sectional view of a gas sensor package 1, according to another embodiment. Unless otherwise noted, the components of FIGS. 12-13 may be the same as or generally similar to like-referenced components of FIGS. 9-10, respectively. For example, in FIG. 12, the package lid 86 can be provided over the sensor die 24 and over other dies (such as Application Specific Integrated Circuit, or ASIC, dies), packages, and/or passive components 80. In FIG. 13, the package lid 86 can be provided over the sensor die 24, and the other dies (e.g., ASIC die(s)), packages, and/or package components 80 can be provided outside the lid 86 and the second chamber 14. Unlike in FIGS. 9-10, however, in FIGS. 12-13, respectively, the sensor die 24 can be inverted as compared with FIGS. 9-10. As shown in FIG. 12, for example, the gas can pass through the gas inlet 50 into the second chamber 14. For example, the gas can pass through openings (not shown) in the die support 87 or dam to enter the second chamber 14.

As illustrated in FIGS. 12 and 13, the encapsulant 41 or glob-top can be disposed over the wire bonds 38. The embodiment of FIG. 13 can be beneficial for capturing the encapsulant 41 within the outer chamber 70 so as to prevent the encapsulant 41 to reach the other dies, packages, and/or passive components 80.

Although this invention has been disclosed in the context of certain embodiments and examples, it will be understood by those skilled in the art that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A gas sensor package comprising:
   a housing including a first chamber and a second chamber;
   an electrolyte in the first chamber;
   a gas inlet to provide fluid communication between the second chamber and the outside environs, the gas inlet configured to permit gas to enter the second chamber from the outside environs; and
   an integrated device die mounted to the housing, the integrated device die comprising a sensor portion having a sensing element configured to detect the gas, the sensor portion of the integrated device die having a first side at least partially exposed to the first chamber and a second side at least partially exposed to the second chamber, the first side opposite the second side; and
   a die cap coupled to the integrated device die, the die cap and integrated device die at least partially defining the first chamber.

2. The package of claim 1, wherein the sensing element comprises at least one of platinum black, ruthenium black, iridium black, carbon, and gold.

3. The package of claim 1, wherein the sensing element is at least partially disposed in the second chamber, wherein the integrated device die comprises a processor portion, the processor portion integrated with the sensor portion.

4. The package of claim 1, further comprising one or more filters provided over the gas inlet.

5. The package of claim 1, wherein the housing further includes an outer chamber, the outer chamber comprises a gas pathway and the gas enters the second chamber through the gas pathway.

6. The package of claim 1, wherein the electrolyte comprises sulfuric acid or a solid electrolyte.

7. The package of claim 1, wherein the integrated device die is partially embedded in a molding compound and the gas inlet is at least partially defined through an aperture of the molding compound.

8. The package of claim 1, wherein the integrated device die at least partially seals the first chamber from the second chamber, wherein the integrated device die comprises a plurality of channels extending from the first side of the integrated device die to the second side of the integrated device die.

9. The package of claim 1, further comprising a package substrate, wherein the integrated device die is mounted over the package substrate.

10. The package of claim 9, further comprising a standoff structure that vertically offsets the integrated device die from the package substrate, wherein the standoff structure comprises lateral channels providing fluid communication between the second chamber and an outer chamber defined by the housing, the second chamber disposed between the integrated device die and the package substrate.

11. The package of claim 9, further comprising a standoff structure that vertically offsets the integrated device die from the package substrate, wherein the first chamber is disposed between the integrated device die and the package substrate.

12. The package of claim 9, further comprising an additional integrated device die mounted to the package substrate.

13. The package of claim 12, wherein the integrated device die is mounted to a die shelf defined by a molding compound over the additional integrated device die, and the second chamber is disposed between the integrated device die and the die shelf.

14. The package of claim 1, wherein the package comprises a package substrate and a package lid mounted to the package substrate, and the second chamber is defined at least in part by the package substrate and the package lid.

15. The package of claim 1, wherein the package comprises a package substrate and a package lid mounted to the package substrate, and the second chamber is defined at least in part between the package substrate and the integrated device die.

16. A gas sensor package comprising:
    a housing defining a first chamber;
    an electrolyte in the first chamber;
    a gas inlet configured to permit gas to enter the gas sensor package from outside environs; and
    an integrated device die mounted to the housing, the integrated device die comprising one or more gas channels and a sensor portion disposed proximate to, and in fluid communication with, the one or more gas channels and having a sensing element configured to detect the gas, the sensor portion of the integrated device die having a first side at least partially exposed to the first chamber and a second side opposite the first side, and
    wherein the gas sensor package is configured such that the gas passes through the one or more gas channels to impinge upon the sensing element.

17. The gas sensor package of claim 16, wherein the housing further defines a second chamber, and the second side of the sensor portion is at least partially exposed to the second chamber.

18. The package of claim 16, further comprising one or more filters between the gas inlet and the sensor portion in a pathway of the gas.

19. A gas sensor package comprising:
    a housing having a gas inlet configured to permit gas to pass through;
    an integrated device die mounted to the housing;
    a die cap mounted to the integrated device die, the die cap at least partially defining a first chamber; and
    an electrolyte in the first chamber,
    wherein the integrated device die comprises a sensor portion having a sensing element configured to detect gas, the sensing element having a first side at least partially exposed to the first chamber and a second side opposite the first side, the second side of the sensing element configured to contact the gas.

20. The package of claim 19, further comprising a package substrate, a package lid mounted to the package substrate, and a second chamber defined at least in part between the package substrate and the integrated device die.

* * * * *